United States Patent
Anderson et al.

(10) Patent No.: US 6,915,700 B2
(45) Date of Patent: *Jul. 12, 2005

(54) PRESS FOR SIMULATING COMPRESSION LOADING OF A POINT SITE ON A WORKPIECE IN A NIP TYPE PROCESS

(75) Inventors: Barry Jay Anderson, Cincinnati, OH (US); Michael Joseph Lamping, Cincinnati, OH (US); Eugene Paul Daut, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/615,977

(22) Filed: Jul. 9, 2003

(65) Prior Publication Data

US 2004/0177709 A1 Sep. 16, 2004

Related U.S. Application Data

(63) Continuation-in-part of application No. 10/377,070, filed on Feb. 28, 2003, and a continuation-in-part of application No. 10/422,879, filed on Apr. 24, 2003.
(60) Provisional application No. 60/429,802, filed on Nov. 27, 2002.

(51) Int. Cl.[7] .................................................. G01L 1/00
(52) U.S. Cl. .......................................... 73/763; 100/48
(58) Field of Search .......................... 73/763, 769, 818, 73/824, 866; 100/48

(56) References Cited

U.S. PATENT DOCUMENTS

| | | | | |
|---|---|---|---|---|
| 4,074,624 A | * | 2/1978 | Biornstad et al. | 100/35 |
| 4,420,958 A | * | 12/1983 | Schulz et al. | 72/21.1 |
| 4,812,722 A | | 3/1989 | Corrothers | |
| 4,854,984 A | | 8/1989 | Ball et al. | |
| 4,919,738 A | | 4/1990 | Ball et al. | |
| 5,167,799 A | * | 12/1992 | Severin et al. | 210/85 |
| 5,188,456 A | | 2/1993 | Burke et al. | |
| 5,351,553 A | | 10/1994 | Lepie et al. | |
| 5,386,092 A | | 1/1995 | Dufrenne | |
| 5,562,027 A | * | 10/1996 | Moore | 100/35 |
| 5,575,078 A | | 11/1996 | Moulton, III | |
| 5,767,402 A | | 6/1998 | Sandlass et al. | |
| 5,974,853 A | * | 11/1999 | Strong et al. | 72/430 |
| 6,145,563 A | | 11/2000 | Kalisiak et al. | |
| 6,248,195 B1 | | 6/2001 | Schmitz | |
| 6,370,962 B1 | | 4/2002 | Sullivan et al. | |
| 6,410,820 B1 | | 6/2002 | McFall et al. | |
| 6,418,828 B1 | | 7/2002 | Kalnitz | |
| 6,500,377 B1 | | 12/2002 | Schneider et al. | |

FOREIGN PATENT DOCUMENTS

EP        1 043 579 A1    10/2000
WO    WO 99/56685 A1    11/1999

OTHER PUBLICATIONS

Merriam–Webster OnLine Dictionary, http://www.m–w.com/cgi–bin/dictionary?book=Dictionary&va=nip, 2 pages.*

* cited by examiner

*Primary Examiner*—Charles Garber
(74) *Attorney, Agent, or Firm*—Jack L. Oney, Jr.; George H. Leal; Jay A. Krebs

(57) ABSTRACT

A simulation press is provided comprising a fixed main body; a carriage associated with the main body for movement relative to the main body; a first plate coupled to the fixed main body and being adapted to engage a workpiece; and a second plate coupled to the carriage for movement with the carriage. The second plate is also adapted to engage the workpiece. One or more motor apparatus are coupled to the fixed main body and the carriage for effecting movement of the carriage relative to the main body. A drive controller is coupled to the motor apparatus for controlling the operation of the motor apparatus in response to feedback from one or more feedback sensors so as to cause the second plate to move relative to the first plate such that the first and second plates engage at least one point site on the workpiece so as to simulate compression loading of a point site on a workpiece in a nip type process.

20 Claims, 20 Drawing Sheets

PRESS FOR SIMULATING COMPRESSION LOADING OF A POINT SITE ON A WORKPIECE IN A NIP TYPE PROCESS

CROSS-REFERENCE TO RELATED APPLICATIONS

This application: 1) claims priority to Provisional Application U.S. Ser. No. 60/429,802, filed Nov. 27, 2002, and entitled RING ROLLING SIMULATION PRESS; 2) is a continuation-in-part of and claims priority to application U.S. Ser. No. 10/377,070, entitled RING ROLLING SIMULATION PRESS, filed on Feb. 28, 2003, which application claims priority to the '802 provisional application; and 3) is a continuation-in-part of and claims priority to application U.S. Ser. No. 10/422,879, entitled A SIMULATION APPARATUS, filed on Apr. 24, 2003, which application claims priority to the '070 non-provisional application and the '802 provisional application; the disclosures of each of the above-identified applications are incorporated herein by reference.

BACKGROUND OF THE INVENTION

It is known in the art to use a press to simulate a low strain activation operation such as the one discussed in published international application WO 99/56685. The press comprised a stationary first plate having first teeth, a second plate having second teeth, a movable ram to which the second plate was coupled, a rotary servo motor coupled to the ram, and a controller for controlling the operation of the rotary servo motor such that the second plate was moved toward the first plate so that a workpiece was engaged by the teeth of the first and second plates. The press did not include sensors of any sort for providing feedback information, such as position or force information concerning the ram, the plates or the motor, to the controller. Nor was the press used to simulate a fusion bonding operation.

U.S. Pat. Nos. 4,854,984 and 4,919,738, the disclosures of which are incorporated herein by reference, disclose a bonding apparatus for bonding portions of plural workpiece layers together, wherein at least one of the workpiece layers comprises a thermoplastic layer. The apparatus comprises a patterned cylinder 22, an anvil cylinder 24, and means 26 for adjustably biasing the cylinders 22 and 24 together. The patterned cylinder 22 is provided with a "saw-tooth shape pattern of protuberances 51 which extend circumferentially about each end of the cylinder," see column 4, lines 65–67 of the '984 patent.

A simulation apparatus is currently unknown which would allow engineers/technicians to quickly and relatively inexpensively test workpieces/web materials to determine the effects of compression loading on a point site of such a workpiece/web material in a nip type process, such as a fusion bonding operation effected using first and second rolls, one of which is provided with a plurality of protuberances. Instead, an apparatus for effecting a nip type process must be constructed, such as an apparatus comprising first and second fusion bonding rolls, so as to allow workpieces to be passed through those rolls to effect a test operation.

Accordingly, there is a need for an apparatus for simulating compression loading of a point site on a workpiece in a nip type process, such as a fusion bonding operation.

BRIEF SUMMARY OF THE INVENTION

This need is met by the present invention, wherein a press is provided for simulating compression loading of a point site on a workpiece in a nip type process, such as a fusion bonding operation. This apparatus allows engineers/technicians to quickly, and relatively inexpensively test workpieces/web materials to determine the effects of compression loading on a point site of such a workpiece/web material in a nip type process. Also provided is a method of simulating compression loading of a point site on a workpiece in a nip type process comprising the steps of: providing a workpiece comprising at least one layer; providing a first plate having a substantially planar surface; providing a second plate having at least one protuberance; and moving one of the first and second plates relative to the other of the first and second plates such that the planar surface and the protuberance compress a point site on the workpiece so as to simulate compression loading of a point site on a workpiece in a nip type process. The first and second plates including the protuberance may be heated to a temperature below the melt temperature of the workpiece to be tested. Further, data collected during a workpiece point site compression loading test can be used to generate a "Load Per Unit Workpiece Point Site Area vs. Percent Compression of the Workpiece Sample" curve.

DETAILED DESCRIPTION OF THE INVENTION

Processes are known, such as the fusion bonding processes disclosed in U.S. Pat. Nos. 4,854,984 and 4,919,738, the disclosures of which are incorporated herein by reference, for effecting compression loading on a plurality of point sites of or discrete locations on a workpiece/web material in a nip type process. Such a process involves passing a workpiece W such as a thermoplastic dual-layer web material through a nip N defined by rolls 22, 24, wherein the first roll 22 is provided with a plurality of protuberances 25, see FIG. 1A. By compressing the workpiece/web material at point sites $W_{PS}$ via the protuberances 25 friction bonds are effected at those sites. That is, the material at each point site $W_{PS}$ is compressed at a sufficient pressure and at a sufficient speed by the protuberances 25 that the material at each point site $W_{PS}$ is caused to flow or melt. If the workpiece/web material comprises two or more layers, those layers are caused to bond to one another at each site. Example workpiece materials comprise thermoplastic webs, films, etc., such as polyethylene webs, films, etc., which materials may comprise a single layer of material having a thickness of from about 0.05 mm to about 5 mm, a dual-layer material having a thickness of from about 0.1 mm to about 10 mm, or a material having three or more layers. In any event, it is preferred that at least a portion of the workpiece W comprise a thermoplastic material.

Figure 1:
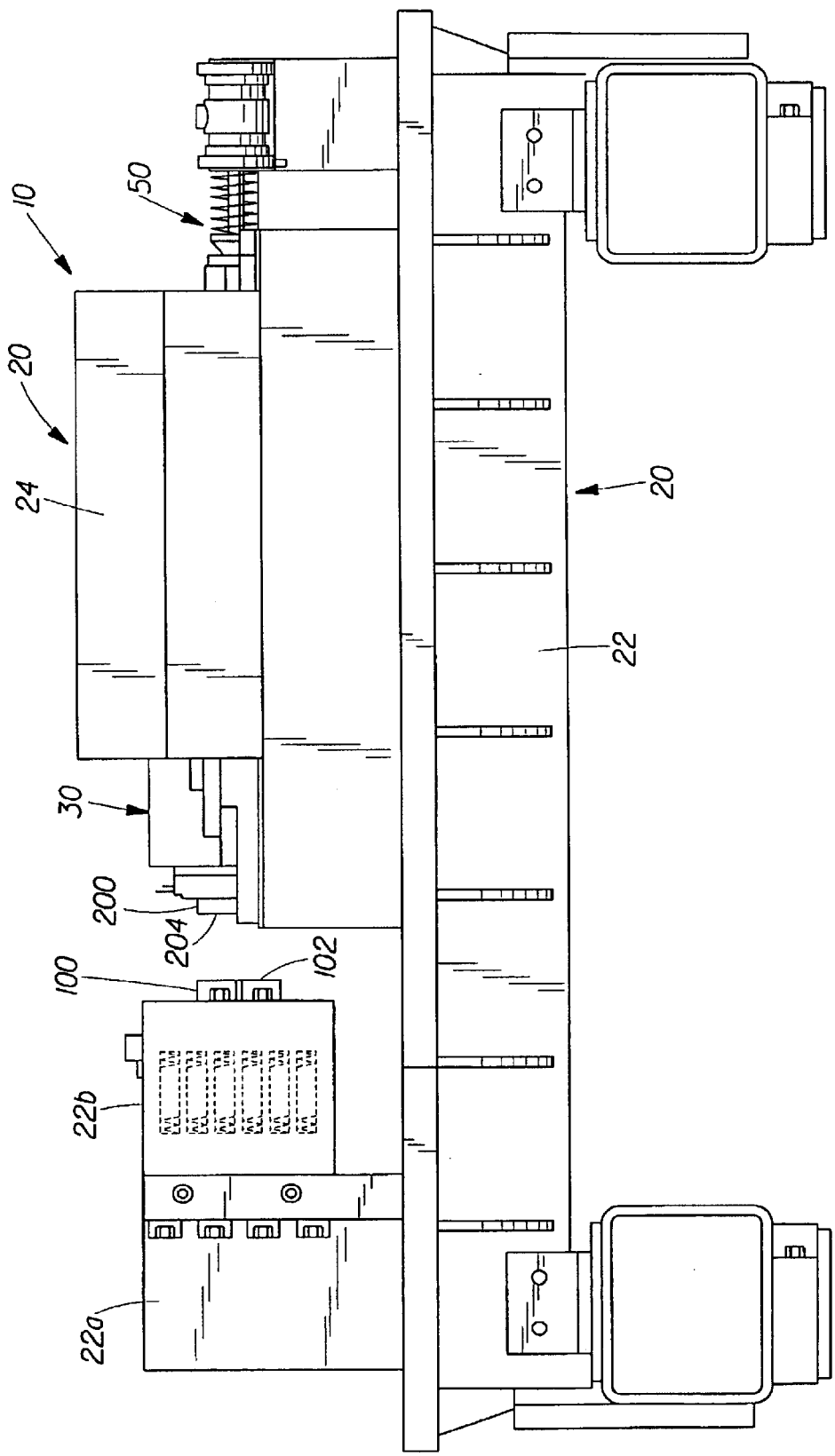
FIG. 1 is a side view of an apparatus of the present invention which functions to replicate work performed by a pair of fusion bonding rolls on a workpiece.

An apparatus 10 constructed in accordance with the present invention is illustrated in FIG. 1 and functions to replicate work performed, for example, by a pair of fusion bonding rolls 22, 24 on a workpiece W. The apparatus 10 comprises a generally stationary first plate 100 having a substantially planar outer surface 102, see FIGS. 1, 5 and 8, and a linearly movable second plate 200 having a protuberance 202 (not shown in FIG. 1) extending from a substantially planar outer surface 204, see FIGS. 2A, 3A and 8. The protuberance 202 has a length in the X direction, see FIG. 8, of from about 0.5 mm to about 10 mm and a distal end 202a having a diameter in the Y direction of from about 1 mm to about 5 mm.

The apparatus 10 of the present invention allows engineers/technicians to quickly and relatively inexpensively test workpieces/web materials to determine the effects of compression loading on a point site of such a workpiece/web material in a nip type process, such as a fusion bonding operation effected using first and second rolls, one of which is provided with a plurality of protuberances.

Figure 2A:
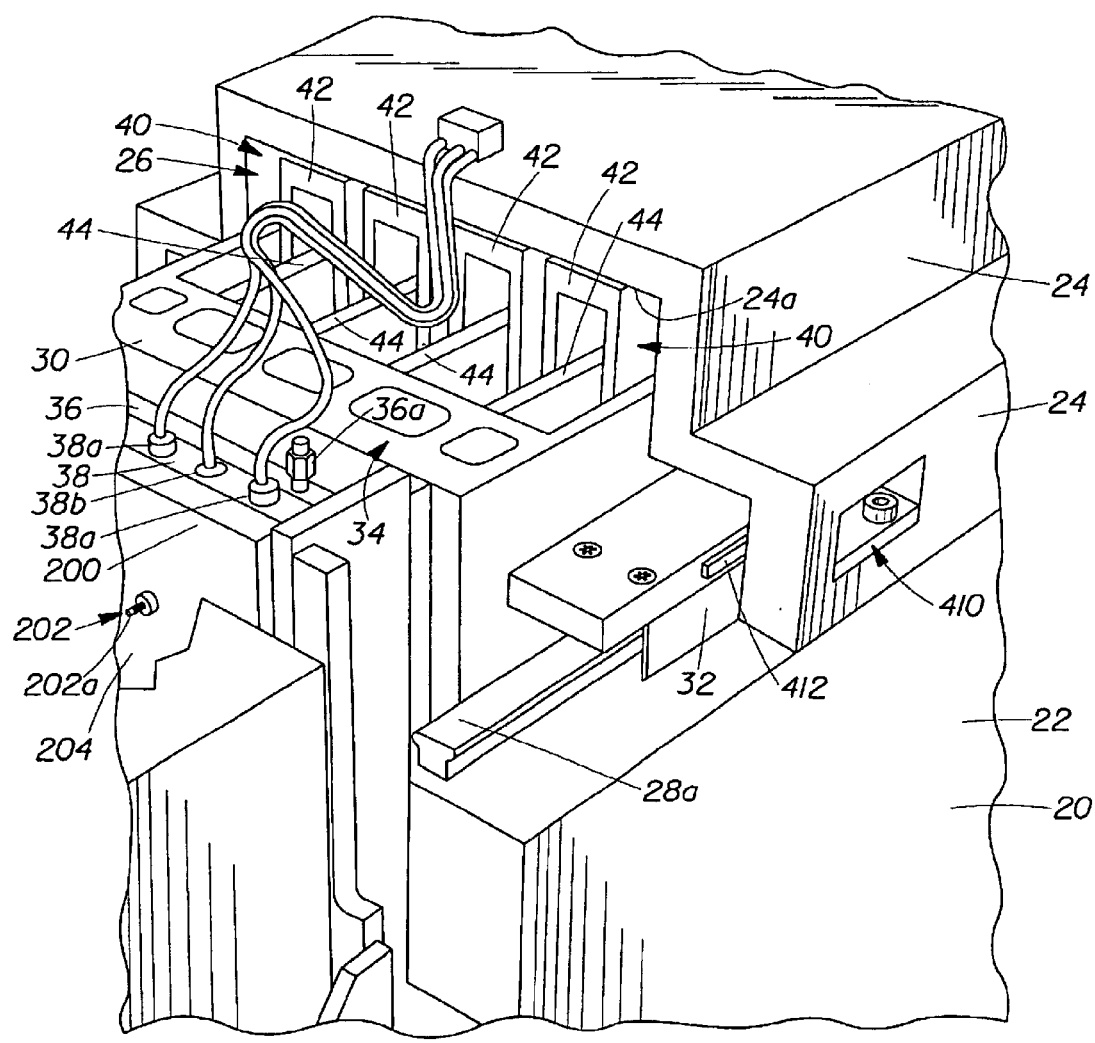
FIG. 2A is a perspective view illustrating a reciprocating carriage provided with a second plate, wherein the carriage is positioned within a cavity defined by the upper and lower portions of a main body of the apparatus.
Figure 2B:
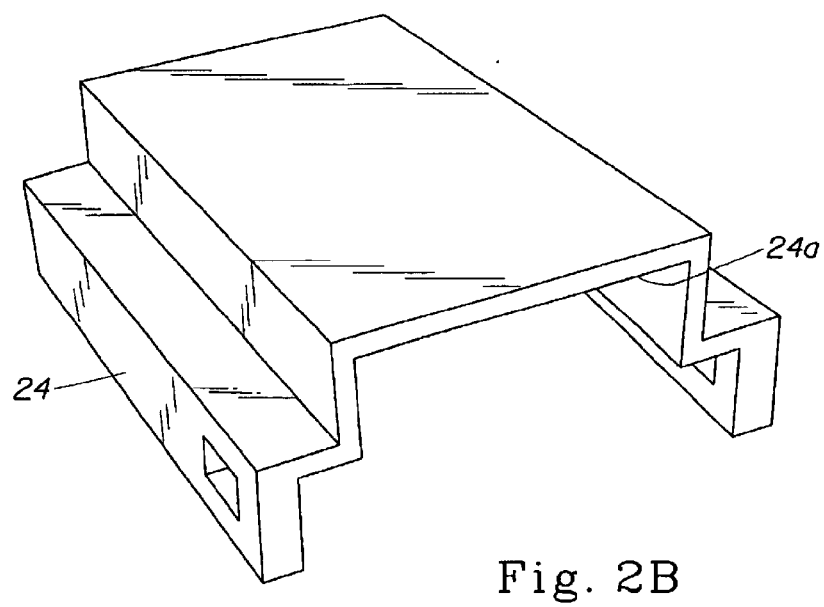
FIG. 2B is a perspective view of the upper portion of the apparatus main body.
Figure 2C:
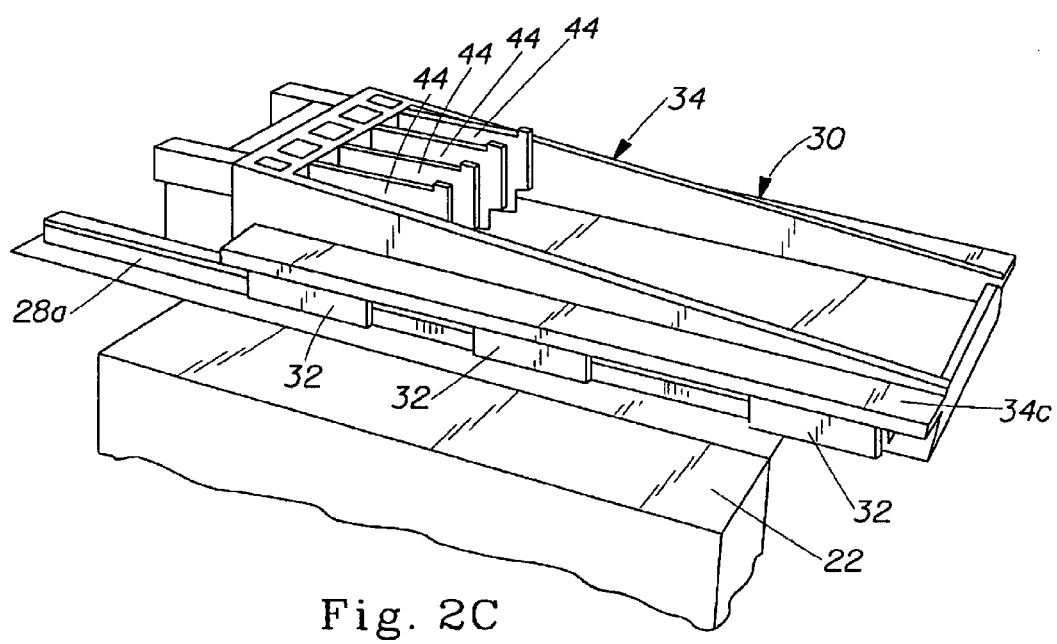
FIG. 2C is a perspective side view of the carriage mounted to the main body lower portion and wherein the main body upper portion and linear servo motors have been removed.
Figure 2D:
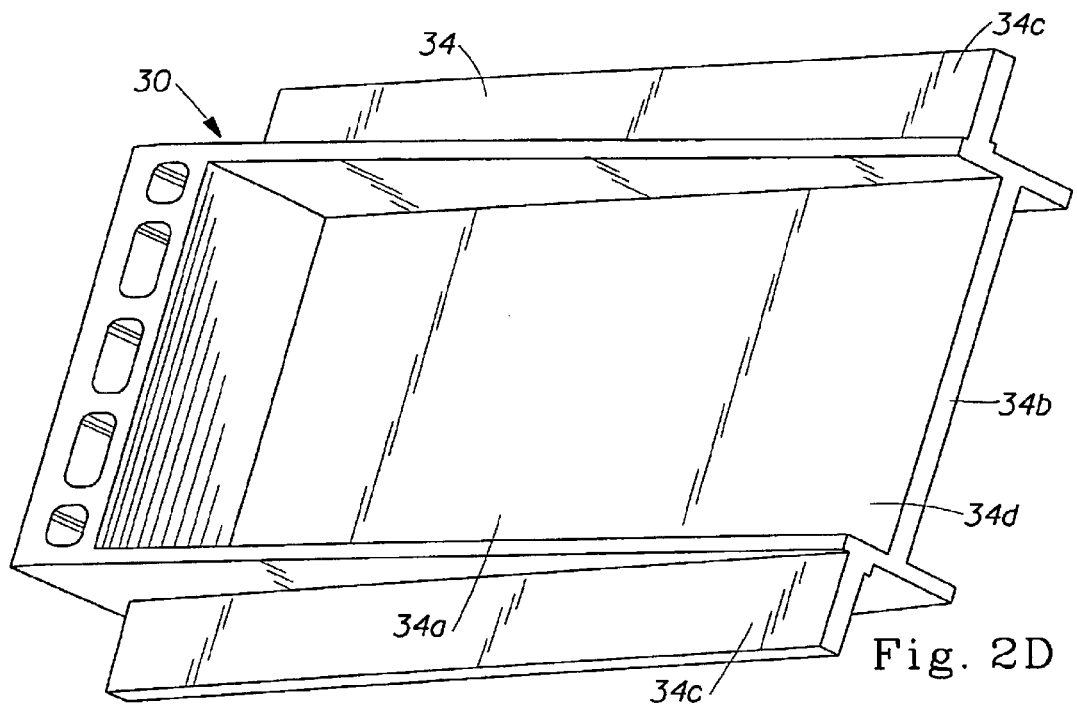
FIG. 2D is perspective view of the carriage main body.
Figure 2E:
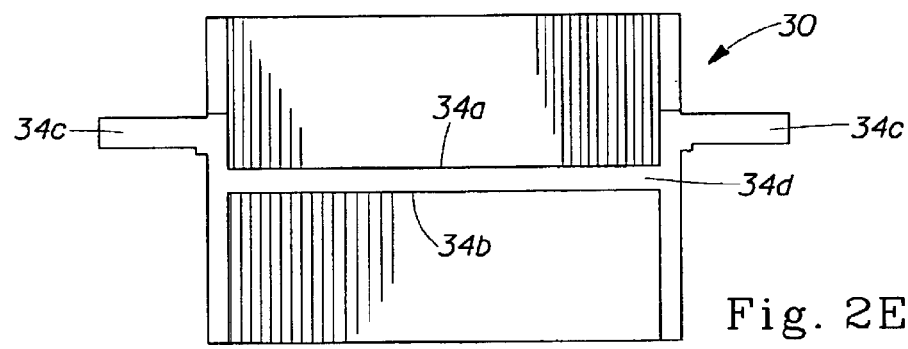
FIG. 2E is a rear view of the carriage main body.
Figure 2F:
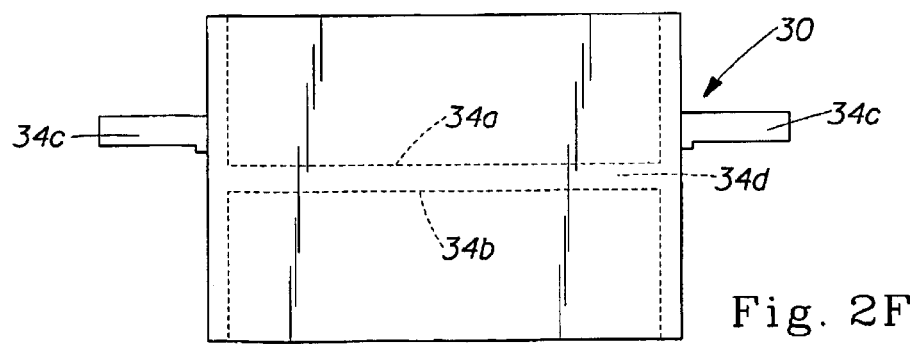
FIG. 2F is a front view of the carriage main body.
Figure 2G:
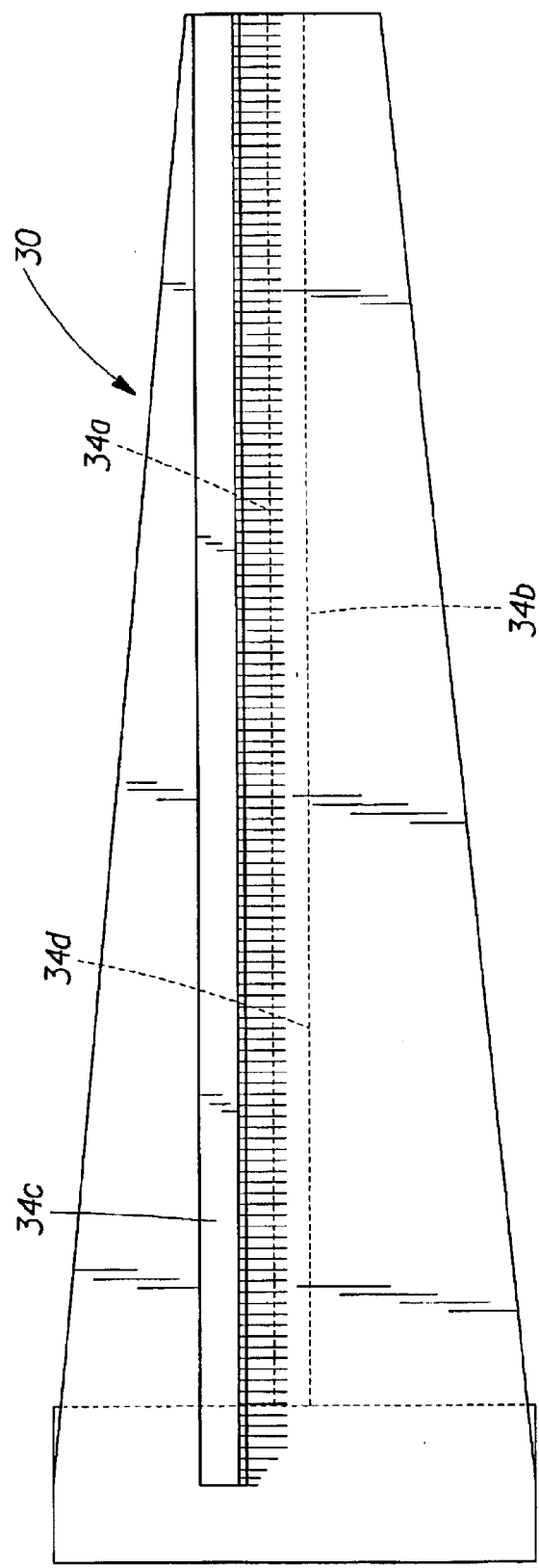
FIG. 2G is a side view of the carriage main body.

The apparatus 10 additionally comprises a fixed main body 20 comprising a lower portion 22 and an upper portion 24 fixedly coupled to the lower portion 22, see FIGS. 1, 2A and 2B. The apparatus 10 further comprises a linearly reciprocating carriage 30 including a main body portion 34 positioned within a cavity 26 defined by the lower and upper portions 22 and 24 of the main body 20, see FIG. 2A, FIG. 2C (in FIG. 2C, the upper portion 24 has been removed from the lower portion 22 to illustrate the carriage 30), and FIGS. 2D–2G (in FIGS. 2D–2G, only the main body portion 34 is illustrated).

Figure 2H:
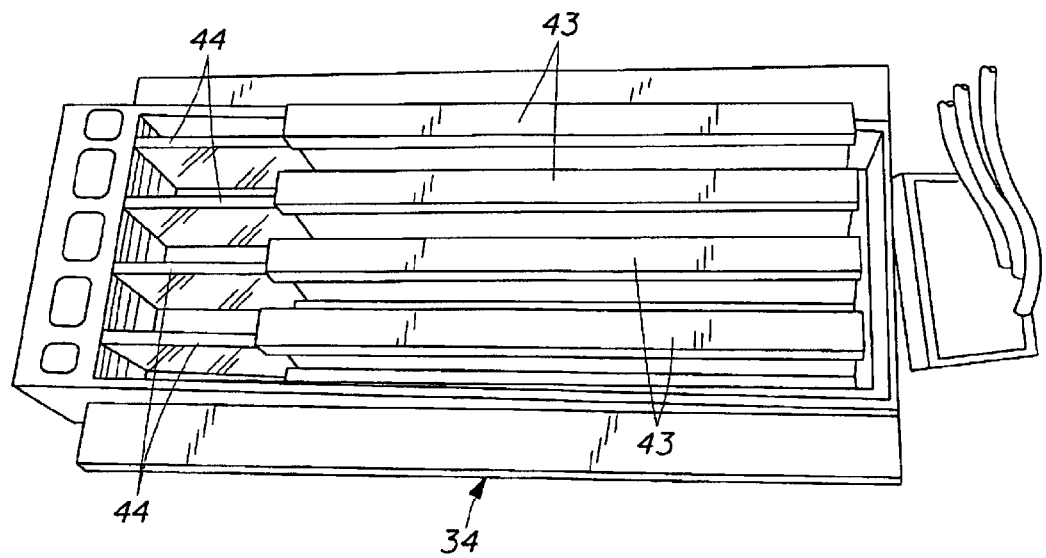
FIG. 2H is a perspective view of the carriage and motor second members.
Figure 2I:
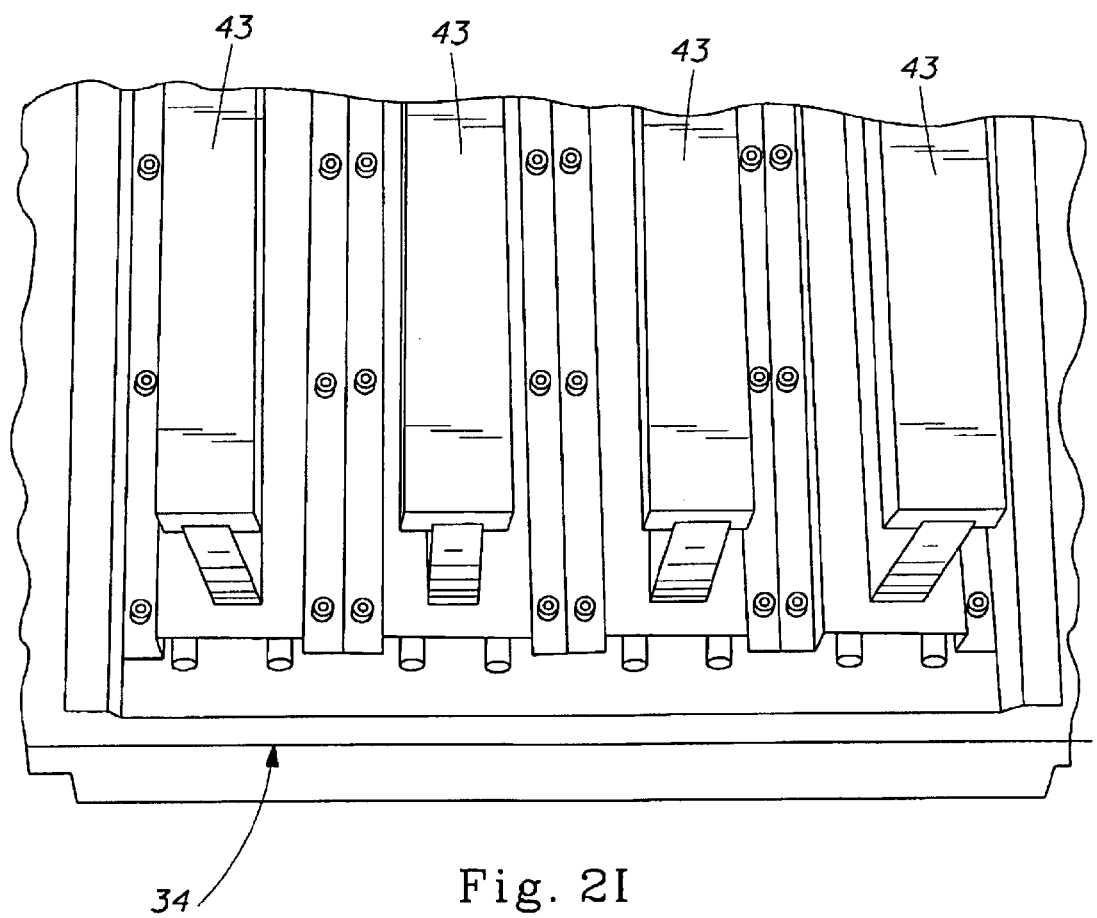
FIG. 2I is a perspective view of a portion of the carriage and motor second members.

The carriage 30 moves along first and second rails 28a and 28b via conventional linear bearings 32 mounted to a pair of wings 34c forming part of the carriage main body portion 34, see FIGS. 2A, 2C, 2D and 3A and 3B. Reciprocating movement of the carriage 30 is effected via eight separate servo linear motors 40 all working in conjunction, which motors 40 are commercially available from Rockwell International Corporation under the product designation "LEC-S-4P." Each servo motor 40 comprises a generally U-shaped first member 42 comprising a metal U-shaped element 42a having a plurality of magnets 42b mounted within and extending substantially the entire length of its U-shaped cavity, see FIGS. 2A and 4, and a movable second member 43 comprising a metal support plate having a plurality of coils wrapped about and extending along the length of the support plate, see FIGS. 2H and 2I. Four of the first members 42 are fixedly coupled to an inner surface 24a of the upper portion 24 of the main body 20, see FIG. 2A, while the remaining four first members (not shown) are fixedly coupled to an upper surface (not shown) of the lower portion 22 of the main body 20 just below the carriage 30. Four of the second members 43 are fixedly coupled to an upper portion 34a of a main plate 34d of the carriage main body portion 34, while the remaining four second members (not shown) are fixedly coupled to a lower portion 34b of the main plate 34d of the carriage main body portion 34. Four polymeric supporting plates 44 are mounted to the upper portion 34a of the main plate 34d, see FIG. 2A, and four polymeric supporting plates (not shown) are mounted to the lower portion 34b of the main plate 34d. The motor second members 43, fixedly coupled to the upper and lower portions 34a and 34b of the main plate 34d of the carriage main body portion 34, are mounted inline with the polymeric plates 44, see FIG. 2H. Upon actuation of the motors 40, each second member 43 moves relative to its corresponding first member 42 such that the carriage 30 linearly moves relative to the fixed main body 20. In the illustrated embodiment, the motors 40 are capable of moving the carriage 30 at a speed up to +/−3 meters/second, and at an acceleration rate up to +/−196 m/s$^2$; and cause the carriage 30 to generate a loading force, i.e., the force applied by the protuberance 202 against a workpiece W and the first plate 100, of up to about +/−20,000 Newtons.

Figure 9:
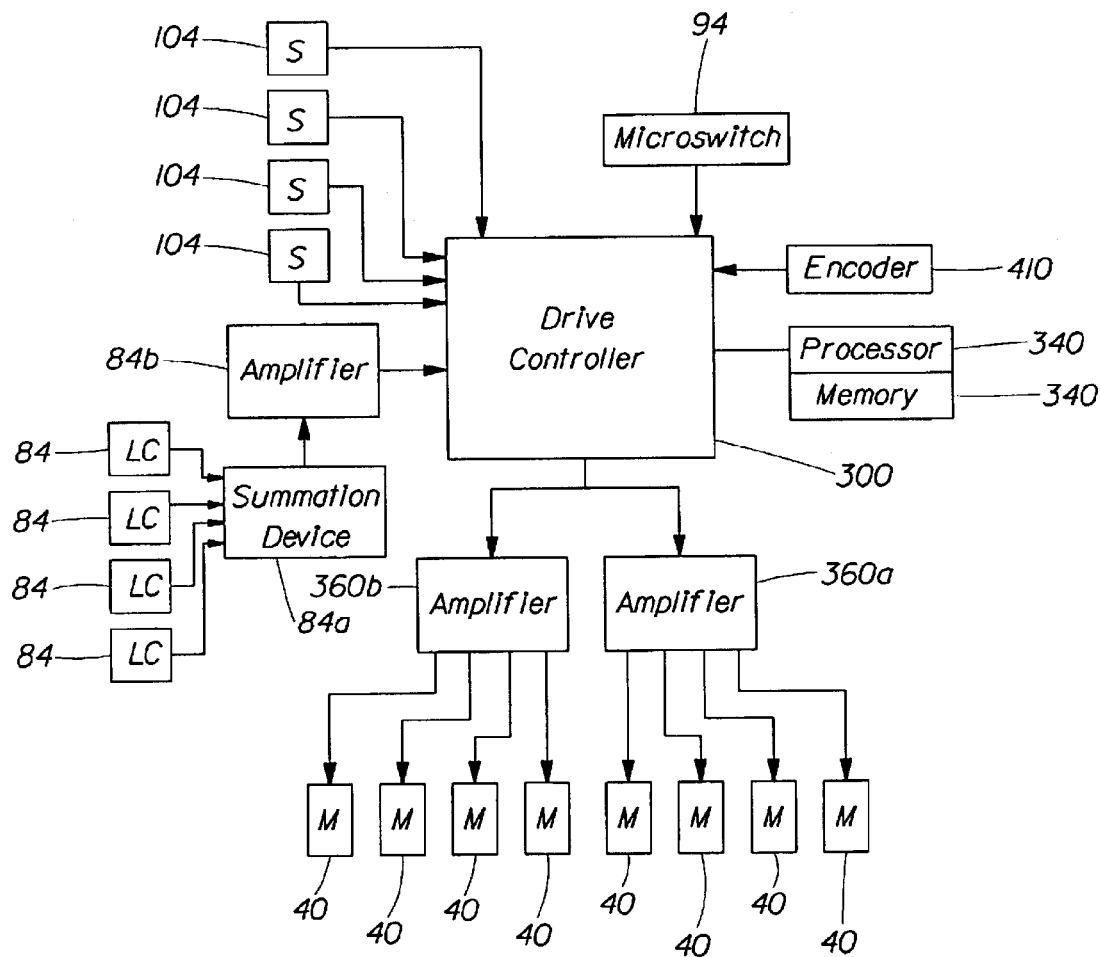
FIG. 9 is a block diagram illustrating a driver controller and amplifiers for driving the motors of the apparatus of FIG. 1.

A drive controller 300, one of which is commercially available from Delta Tau Corporation under the product designation "Turbo PMAC 2-PC," is provided for controlling the operation of the motors 40, see FIG. 9. The drive controller 300 generates a drive signal, which is received by first and second amplifiers 360a and 360b. The amplifiers 360a and 360b are commercially available from Delta Tau Corporation under the product designation "Quad Amp."

Each amplifier 360*a*, 360*b* is connected to four servo motors 40. In response to receiving the drive signal from the controller 300, each amplifier 360*a*, 360*b* generates substantially the same drive control signal to its corresponding four motors 40.

The position of the carriage 30 relative to the fixed main body 20 is sensed via a linear encoder read head 410 coupled to the upper portion 24 of the fixed main body 20, see FIGS. 2A, which reads a position value from a corresponding sensor strip 412 mounted to the carriage 30 for movement with the carriage 30.

Figure 3A:
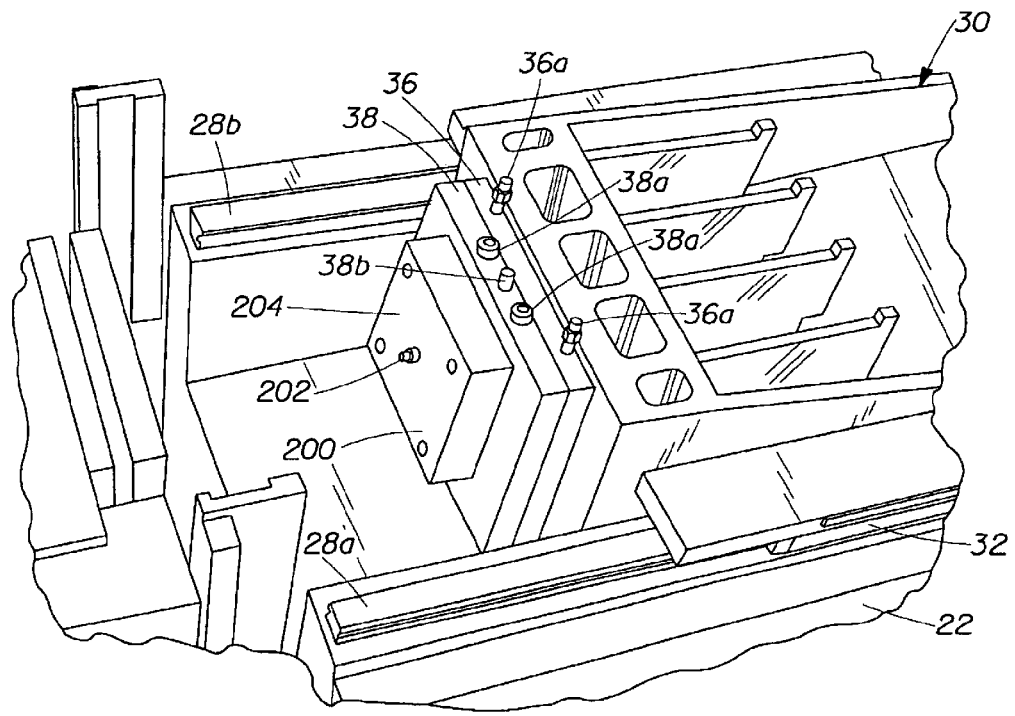
FIG. 3A is a perspective view of a portion of the carriage and the second plate mounted to the carriage.
Figure 3B:
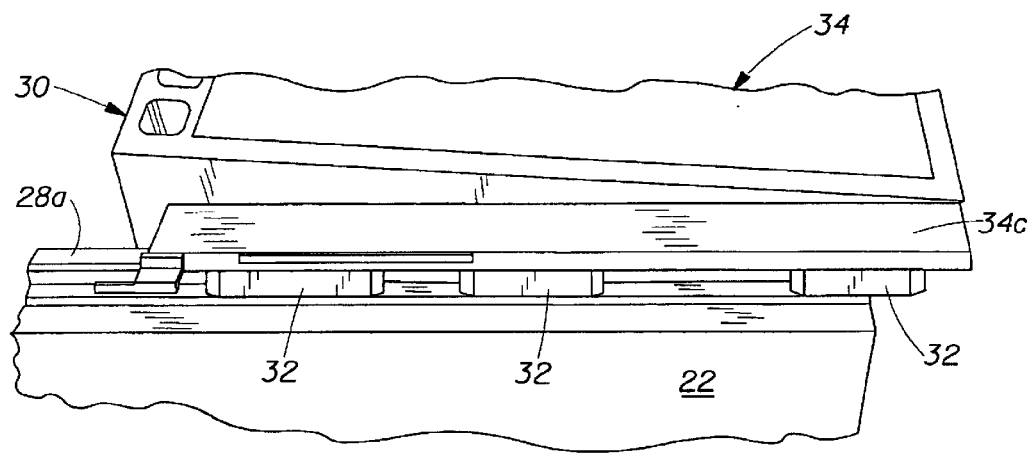
FIG. 3B is a side, perspective view of a portion of the carriage and a portion of the main body lower portion.
Figure 4:
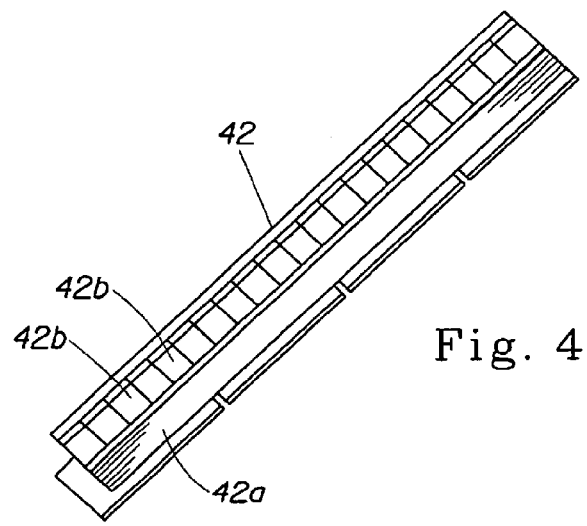
FIG. 4 is a perspective view of a U-shaped first member of one of the servo linear motors in the apparatus of FIG. 1.
Figure 8:
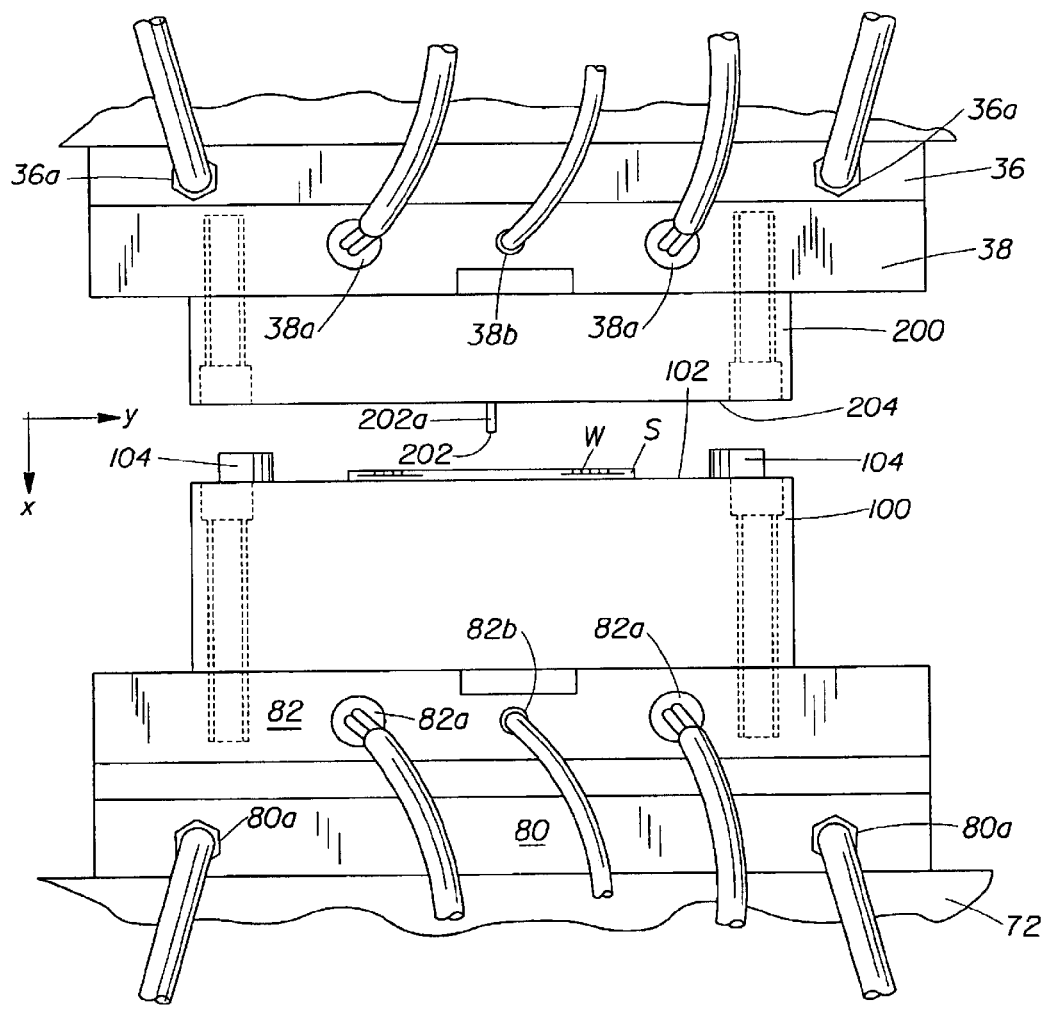
FIG. 8 is a top view of the first and second plates, wherein a workpiece sample S is secured to the first plate.
Figure 9A:
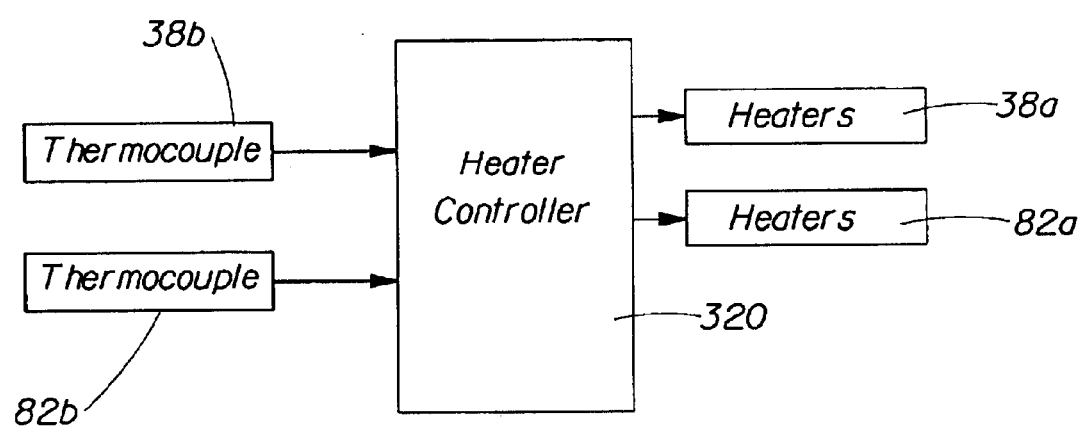
FIG. 9A is a block diagram illustrating a heater controller of the present invention.

The carriage 30 further comprises a cooled plate 36 and a heated plate 38, see FIGS. 2A, 3A and 8. The second plate 200 is mounted, such as bolts, directly to the heated plate 38. The plate 38 is heated via a pair of resistive heaters 38*a*, see FIGS. 2A and 3A. The temperature of the plate 38 is detected via a thermocouple 38*b*, which generates temperature signals to a heater controller 320, see FIGS. 2A and 9A. The heater controller 320 controls activation of the resistive heaters 38*a* so as to maintain the plate 38 at a desired temperature, e.g., from about ambient temperature to about 160° C. The cooled plate 36 is cooled via air circulating through the plate 36. The air is provided to the plate 36 via a pair of air lines coupled to the plate 36 via fittings 36*a*, see FIG. 3A. The cooled plate 36 reduces energy in the form of heat from being transferred from the heated plate 38 to the carriage main body portion 34.

A pair of spring-biased rear bumpers 50 are provided to limit the travel of the carriage 30 in a direction away from the first plate 100, see FIG. 1.

Referring again to FIG. 1, the lower portion 22 of the main body 20 comprises an outer support member 22*a*. Extending through the support member 22*a* are, in the illustrated embodiment, four threaded bores (not shown), each provided with a corresponding threaded rod 60, see FIGS. 6 and 7. Fixedly coupled to the outer support member 22*a* are a pair of L-shaped position limiting members 22*b* and 22*c*. A spring-loading plate 70 is received between the members 22*b* and 22*c* and abuts against the threaded rods 60. A spring-loaded base plate 72 is also received between the members 22*b* and 22*c* and is biased against arm portions 22*d* of the limiting members 22*b* and 22*c* via a plurality of compression springs 74, see FIGS. 5–7 and 6A. A pair of alignment rods 72*a* extend from the plate 72 and pass through linear bearings 70*a* provided in the spring-loading plate 70 as well as linear bearings (not shown) provided in the support member 22*a*, see FIG. 7. The springs 74 are mounted on corresponding rods extending from the spring-loaded plate 72. Bores are provided in the spring-loading plate 70 for receiving the rods about which the springs 74 are mounted. The position of the spring-loading plate 70 can be varied via adjustment of the positions of the threaded rods 60 so as to adjust the biasing force applied by the springs 74 against the plate 72. In the illustrated embodiment, approximately twelve (12) springs 74 are provided for applying approximately 7000 pounds (31,000 N) of force against the spring-loaded plate 72.

A cooled plate 80 is fixedly coupled to the spring-loaded plate 72 via bolts (not shown), see FIGS. 5–7 and 6A. A heated plate 82 is fixedly mounted to the cooled plate 80 via preload screws. Positioned between the cooled plate 80 and the heated plate 82 are a plurality of piezoelectric load cells 84, four in the illustrated embodiment, see FIG. 6A and 7, which are commercially available along with the preload screws for joining the heated plate 82 to the cooled plate 80 from Kistler Instrument Corporation under the product designation "Load Washer and Preload Screw, Model No. 9031." Signals generated by the load cells 84 are provided to a summation device 84*a*, see FIG. 9, which is commercially available from Kistler Corporation under the product designation "4-Gang Connector, Model No. 107B." The summation device 84*a* functions to combine the signals generated by the four load cells 84 and generate a single force signal to an amplifier 84*b*. The amplifier 84*b* is commercially available from Kistler Corporation under the product designation "Dual Charge Amplifier, Model No. 5010B." An amplified force signal is generated by the amplifier 84*b* to the controller 300 and is representative of the combined force directly applied to the load cells 84 by the cooled plate 80 as a result of the first and second plates 100 and 200 engaging a web material sample S. The preload screws coupling the heated plate 82 to the plate 80 extend through center bores in the load cells 84.

Figure 5:
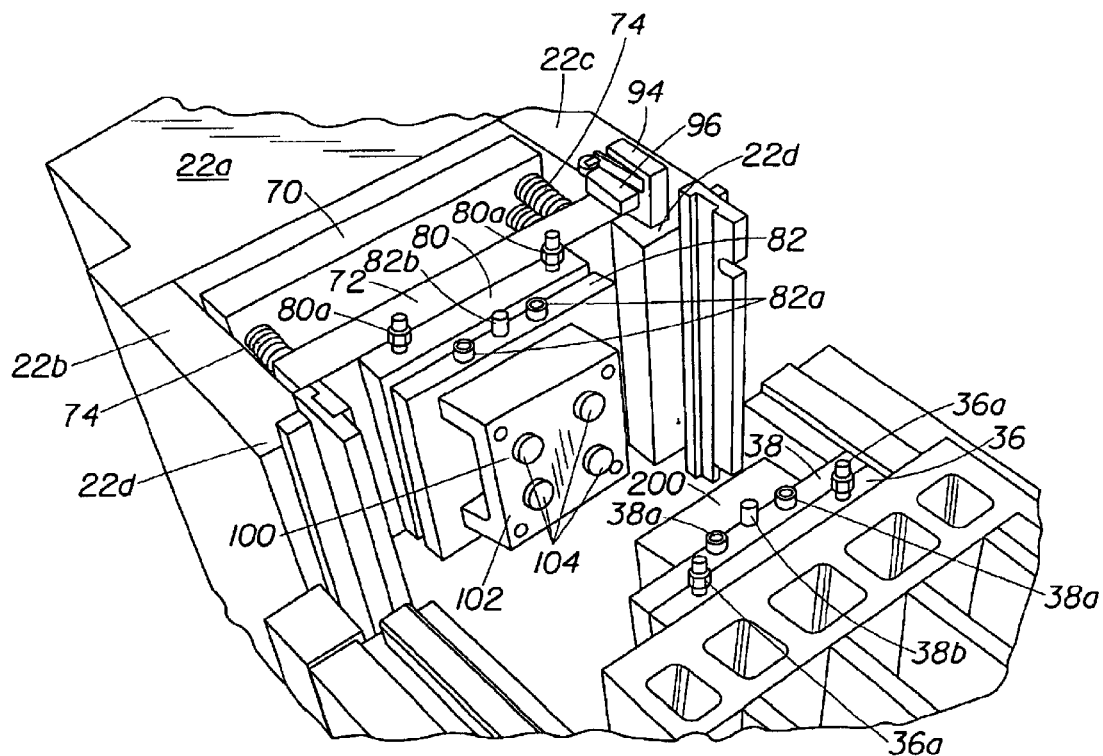
FIG. 5 is a perspective view of an outer support member of the apparatus main body, L-shaped position limiting members; a spring-loading plate, a spring-loaded plate, a heated plate, a cooled plate and a first plate of the apparatus illustrated in FIG. 1.
Figure 6:
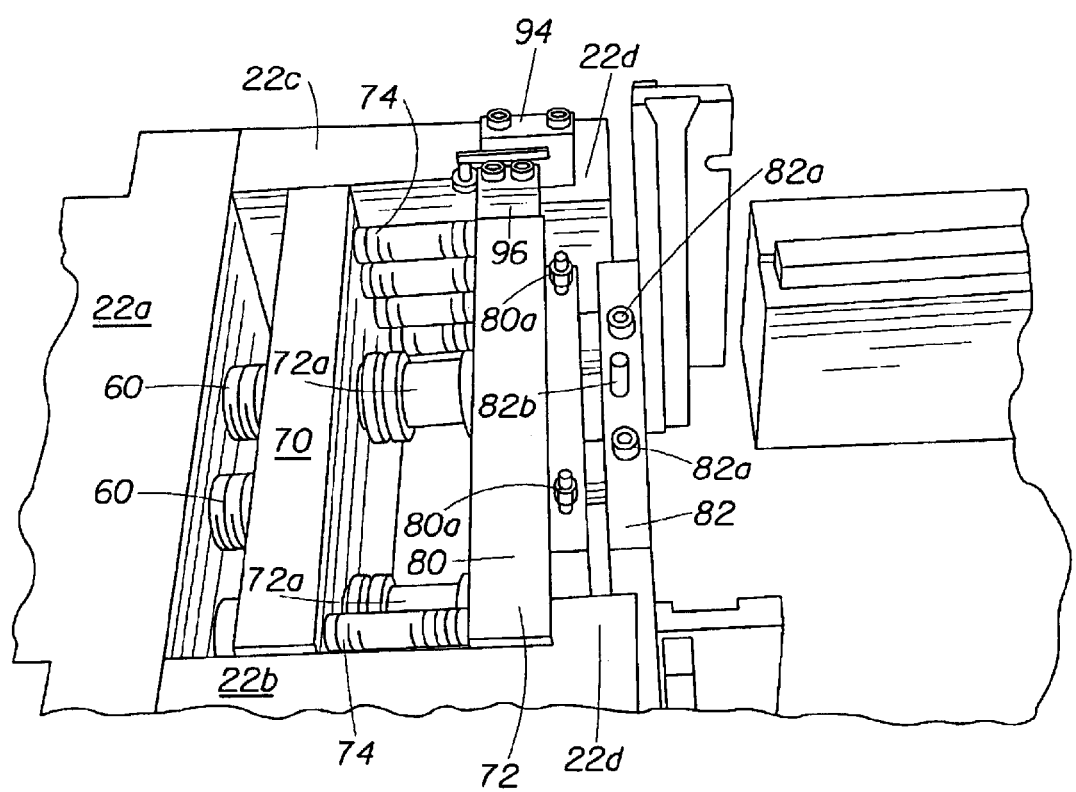
FIGS. 6 and 7 are perspective views of the outer support member of the apparatus main body, the L-shaped position limiting members, the spring-loading plate, the spring-loaded plate, the heated plate, and the cooled plate and, wherein the stationary first plate is not illustrated.
Figure 6A:
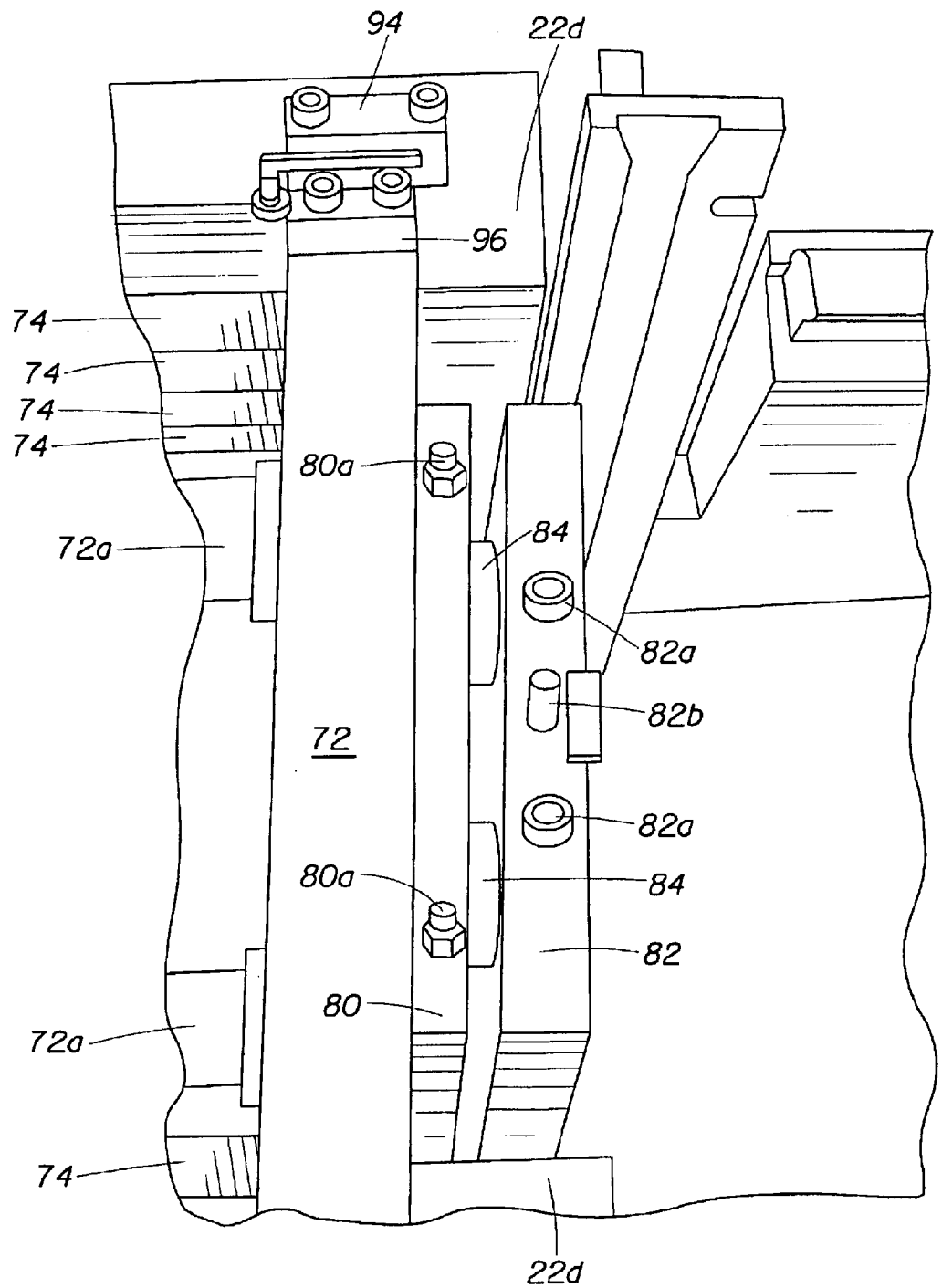
FIG. 6A is a perspective view of portions of the L-shaped position limiting members; the spring-loaded plate, the heated plate, and the cooled plate and, wherein the stationary first plate is not illustrated.
Figure 7:
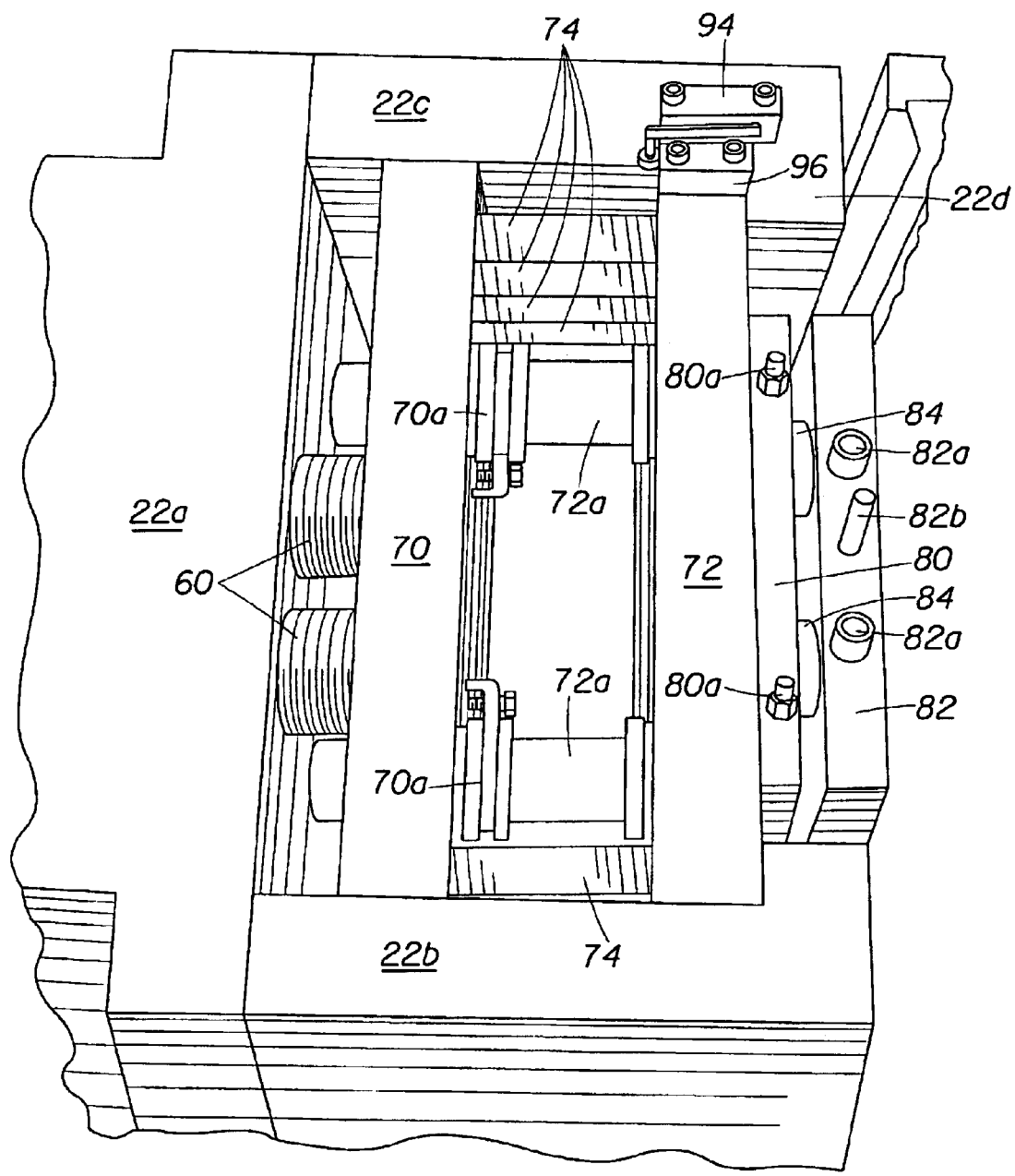

The first plate 100, illustrated in FIG. 5 but not shown in FIGS. 6, 7 and 6A, is mounted, such as by bolts (not shown), directly to the heated plate 82. The plate 82 is heated via a pair of resistive heaters 82*a*, see FIGS. 5, 6 and 6A. The temperature of the plate 82 is detected via a thermocouple 82*b*, which generates temperature signals to the controller 320, see FIGS. 6, 6A and 9A. The heater controller 320 controls activation of the resistive heaters 82*a* so as to maintain the plate 80 at a desired temperature, e.g., from about ambient temperature to about 160° C. The cooled plate 80 is cooled via air circulating through the plate 80. The air is provided to the plate 80 via a pair of air lines coupled to the plate 80 via fittings 80*a*. The cooled plate 80 reduces energy in the form of heat from being transferred from the heated plate 82 to the spring-loaded plate 72.

To prevent damage to the first and second plates 100 and 200 due to over travel of the carriage 30 towards the first plate 100, a sensor arrangement is provided. It comprises a microswitch 94 mounted to the limiting member 22*c* and an actuator 96 fixedly mounted to the spring-loaded plate 72, see FIGS. 6 and 7. The microswitch 94 is coupled to the controller 300, see FIG. 9. If over travel of the carriage 30 occurs, the protuberance 202 on the second plate 200 will engage the first plate 100. When the force applied by the protuberance 202 against the first plate 100 and, hence, against the spring-loaded plate 72 exceeds the biasing force applied by the compression springs 74 against the plate 72, the plate 72 will move in a direction toward the spring-loading plate 70 causing the actuator 96 to actuate the switch 94, which, in turn, generates a corresponding signal to the controller 300. In response, the controller 300 disconnects power to the motors 40 driving the carriage 30.

During a fusion bonding operation, each protuberance 25 and a corresponding section 24*a* of the engaging or second roll 24, see FIG. 1A, compresses a point site $W_{PS}$ on a workpiece W a sufficient amount, to a sufficient temperature below the workpiece material melt point temperature and at a sufficient speed so as to cause the material at the point site $W_{PS}$ to flow or melt. If the workpiece W comprises two or more layers of material, those layers are bonded together. It is noted that during the fusion bonding operation, the protuberance 25 and the corresponding section 24*a* may be at a temperature substantially equal to ambient temperature or heated to a temperature above ambient, e.g., up to about 160° C.

Figure 1A:
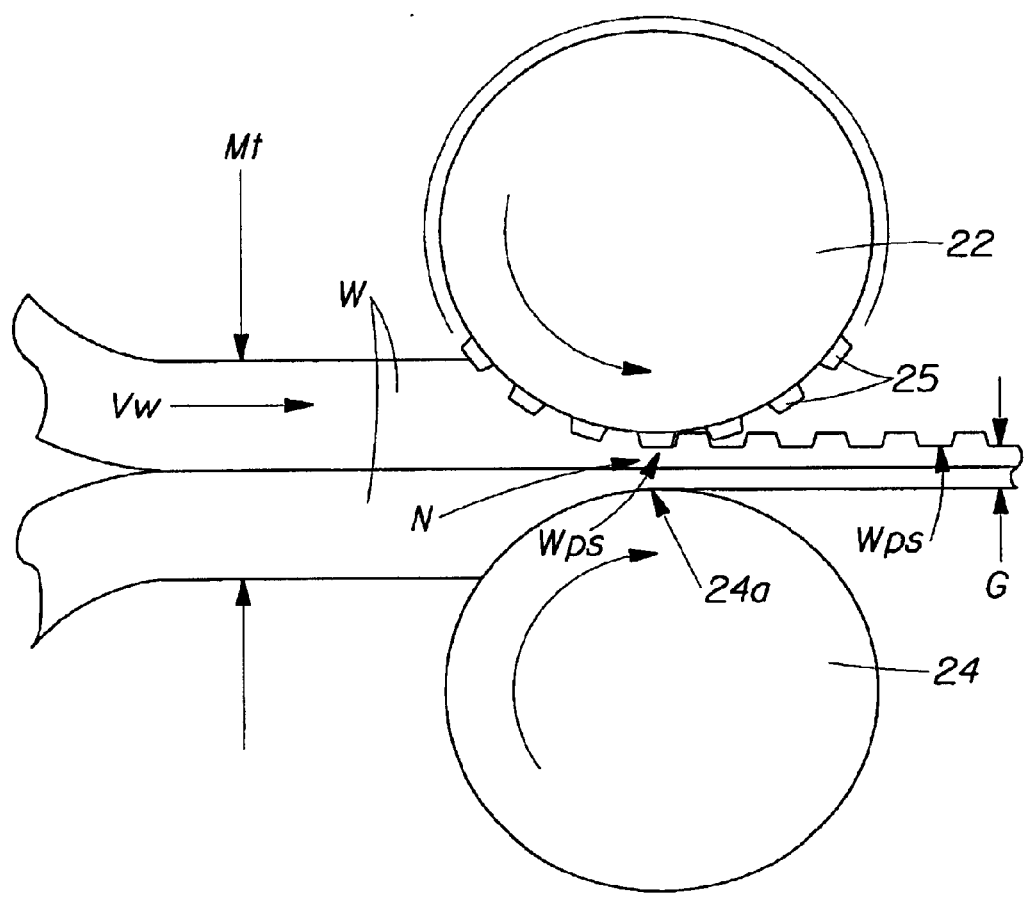
FIG. 1A is a schematic view of first and second rolls effecting a fusion bonding operation.

A point site $W_{PS}$ on a workpiece W, such as a web of material, moves at a velocity Vw through a nip N defined by the rolls 22, 24 and is engaged by a protuberance 25 and a corresponding section 24*a* of the second roll 24 for a time period 2T as it moves through the nip N. One-half of the total engagement time that the given point site $W_{PS}$ on the workpiece W is engaged by the protuberance 25 and the corresponding section 24a of the second roll 24 can be determined via the following equation:

$$T = T_1 = T_2 = a\cos\left[1 - \frac{E_M}{Di}\right] \cdot \left[\frac{Di}{2 \cdot Vw}\right]$$

where:

$E_M$ is equal to the amount by which the point site $W_{PS}$ is compressed from an initial thickness $M_T$ to a final thickness G by the protuberance 25 and the corresponding section 24a of the second roll 24, see FIG. 1A;

Di is equal to the diameter of the first and second rolls 22 and 24 (it is presumed that the rolls 22 and 24 have the same diameter; it is further presumed that the lengths of a pair of protuberances 25 are included in the diameter of roll 22); and and Vw is equal to the workpiece velocity.

The initial position Pi1 of a protuberance 25 on the roll 22 relative to a corresponding section 24a on the second roll 24 when the protuberance 25 first makes contact with the workpiece W, which is equal to the initial position of the protuberance 202 on the second plate 200 of the apparatus 10 relative to the outer surface 102 on the first plate 100 when the protuberance 202 first makes contact with the workpiece W, can be determined by the following equation:

$$Pi1 = G + Di \cdot \left[1 - \cos\left[a\cos\left(1 - \frac{E_M}{Di}\right) \cdot (-1)\right]\right]$$

where:

$E_M$ is equal to the amount by which the point site $W_{PS}$ is compressed by the protuberance 25 and the corresponding section 24a of the second roll 24 and is also equal to the amount by which the point site $W_{PS}$ is compressed by the protuberance 202 of the second plate 200 and the outer surface 102 of the first plate 100;

Di is equal to the diameter of the first and second rolls 22 and 24; and and G is equal to the final compressed thickness of the workpiece point site $W_{PS}$, see FIG. 1A.

The initial protuberance velocity Vi1 of a protuberance 25 on the roll 22 relative to a corresponding section 24a on the second roll 24 when the protuberance 25 first makes contact with the workpiece W, which is equal to the initial velocity of the protuberance 202 on the second plate 200 of the apparatus 10 relative to the outer surface 102 on the first plate 100 when the protuberance 202 first makes contact with the workpiece W, can be determined by the following equation:

$$Vi1 = +Di \cdot \sin\left[a\cos\left(1 - \frac{E_M}{Di}\right) \cdot (-1)\right] \cdot \left[\frac{a\cos\left(1 - \frac{E_M}{Di}\right)}{T}\right]$$

where:

$E_M$ is equal to the amount by which the point site $W_{PS}$ is compressed by the protuberance 25 and the corresponding section 24a of the second roll 24 and is also equal to the amount by which the point site $W_{PS}$ is compressed by the protuberance 202 of the second plate 200 and the outer surface 102 of the first plate 100;

Di is equal to the diameter of the first and second rolls 22 and 24; and and T is equal to one-half of the total engagement time that a point site $W_{PS}$ on the workpiece W is engaged by a first roll protuberance 25 and the corresponding section 24a of the second roll 24, which is equal to one-half of the total engagement time that a point site $W_{PS}$ on the workpiece W is engaged by the protuberance 202 on the second plate 200 and the outer surface 102 of the first plate 100.

The initial protuberance acceleration Ai1 of a protuberance 25 on the roll 22 relative to a corresponding section 24a on the second roll 24 when the protuberance 25 first makes contact with the workpiece W, which is equal to the initial acceleration of the protuberance 202 on the second plate 200 of the apparatus 10 relative to the outer surface 102 on the first plate 100 when the protuberance 202 first makes contact with the workpiece W, can be determined by the following equation:

$$Ai1 = +Di \cdot \cos\left[a\cos\left(1 - \frac{E_M}{Di}\right) \cdot (-1)\right] \cdot \left[\frac{a\cos\left(1 - \frac{E_M}{Di}\right)}{T}\right]^2$$

where:

$E_M$ is equal to the amount by which the point site $W_{PS}$ is compressed by the protuberance 25 and the corresponding section 24a of the second roll 24 or the amount by which the point site $W_{PS}$ is compressed by the protuberance 202 of the second plate 200 and the outer surface 102 of the first plate 100;

Di is equal to the diameter of the first and second rolls 22 and 24; and and T is equal to one-half of the total engagement time that a point site $W_{PS}$ on the workpiece W is engaged by the protuberance 25 and the corresponding section 24a of the second roll 24 or one-half of the total engagement time that a point site $W_{PS}$ on the workpiece W is engaged by the protuberance 202 on the second plate 200 and the outer surface 102 of the first plate 100.

A fusion bonding process is simulated by the apparatus 10 of the present invention in the following manner.

Prior to running the simulation, an engineer/technician defines the following parameters concerning the fusion bonding operation to be simulated: a desired workpiece velocity Vw, i.e., the velocity at which the workpiece W would run if passed between a pair of first and second rolls 22 and 24; the diameter Di of the first and second rolls 22, 24; and an amount $E_M$ by which a point site $W_{PS}$ is compressed by a first roll protuberance 25 and the corresponding section 24a of the second roll 24, i.e., the workpiece initial thickness $M_T$—the workpiece final thickness G.

As noted above, the first plate 100 is provided with a substantially planar outer surface 102 and the second plate 200 is provided with a protuberance 202 extending from a substantially planar outer surface 204, see FIGS. 2A, 3A, 5 and 8.

A substantially rectangular sample S of a workpiece W to be tested is secured, such as by tape (not shown), to the outer surface 102 of the first plate 100, see FIG. 8. The workpiece W may comprise one or more layers, may have a combined thickness, i.e., the thickness of all layers combined, of from about 0.05 mm to about 10 mm, and may comprise a thermoplastic material. Prior to engaging the workpiece sample S with the protuberance 202, the sample S may be heated to a predefined temperature, e.g., of from about ambient temperature to about 160° C., by moving the carriage 30 to a position such that the protuberance 202 on the second plate 200 is positioned just adjacent to the workpiece sample S. As noted above, the heater controller 320 maintains the heated plates 38 and 82 at a predefined temperature. The sample S can be heated to a desired temperature by maintaining the sample S between the first and second plates 100 and 200 for a predefined period of time with the heated plates 38 and 82 controlled to a predetermined temperature.

The drive controller 300 controls the operation of the servo linear motors 40 in accordance with feedback generated by the load cells 84 and the linear encoder read head 410, see FIG. 9. The controller 300 causes the motors 40 to drive the carriage 30 from a home position toward the first plate 100 such that the second plate protuberance 202 in conjunction with the first plate outer surface 102 compresses a point site $W_{PS}$ on the sample S to a desired thickness G. Once the second plate 200 has been moved to a predefined position relative to the first plate 100 so as to allow the protuberance 202 and the first plate 100 to compress the point site $W_{PS}$ to the desired thickness G, the controller 300 then causes the motors 40 to drive the carriage 30 in a direction away from the first plate 100 such that the protuberance 202 on the second plate 200 disengages from the workpiece sample S and, further, such that the carriage 30 returns to its home position. In the illustrated embodiment, movement of the carriage 30 from its home position to a position where the protuberance 202 on the second plate 200 is positioned at a predefined inward-most location spaced from the first plate outer surface 102 is separated into four discrete segments: a forward acceleration segment; a forward linear segment; a forward transition segment; and an engagement segment. Further, movement of the carriage 30 from the position where the protuberance 202 on the second plate 200 is positioned at a desired location spaced from the first plate outer surface 102 back to its home position is separated into four discrete segments: a disengagement segment; a reverse transition segment; a reverse linear segment; and a reverse acceleration segment.

Each of the eight segments comprises a plurality of equal discrete time intervals, e.g., 300 microseconds. For example, the total time period required for execution of the eight segments is determined and this total time period is then divided by a predefined number of control points the drive controller 300 is capable of processing during a fusion bonding simulation operation, e.g., 7990, so as to determine the period for the discrete time intervals (also referred to herein as a first time period $TP_1$). If the calculated period for the discrete time intervals is less than a predefined value, e.g., 300 micro-seconds, the predefined value is used.

Using equations corresponding to the eight segments, to be discussed below, a processor/memory unit 340 determines, for each discrete time interval within each segment, a corresponding position for the carriage 30. The time intervals and corresponding carriage positions are provided to the drive controller 300. During the forward acceleration segment, the forward linear segment, the forward transition segment, the reverse transition segment, the reverse linear segment and the reverse acceleration segment, the drive controller 300 generates appropriate drive signals to the amplifiers 360a, 360b to control the movement of the carriage 30 based on the corresponding, predefined carriage positions, and in response to carriage position signals from the linear encoder read head 410. During the engagement and disengagement segments, the drive controller 300 generates appropriate drive signals to the amplifiers 360a, 360b to control the movement of the carriage 30 based on the corresponding, predefined carriage positions, and in response to carriage position signals from the linear encoder read head 410 and force signals from the amplifier 84b.

The carriage 30 is positioned at its "0 position" when the distal end 202a of the second plate protuberance 202 first makes contact with the first plate outer surface 102. The engagement segment is defined as occurring when the carriage 30 is positioned away from its "0 position" a distance equal to a maximum workpiece sample thickness or caliper that the apparatus 10 is capable of testing, until the protuberance distal end 202a is positioned a desired inward-most distance from the first plate outer surface 102 such that a point site $W_{PS}$ on a workpiece sample S is compressed to a desired thickness G. The disengagement segment is defined as occurring when the carriage 30 reverses its direction so as to move the second plate 200 away from the first plate 100 until the carriage 30 reaches a distance away from its "0 position" equal to the maximum workpiece sample thickness. The processor/memory unit 340 calculates a carriage position, a protuberance velocity and a protuberance acceleration for each of a plurality of equal discrete time intervals occurring during the engagement and disengagement segments as follows. The protuberance velocity and acceleration values are calculated for the engagement and disengagement segments by the processor/memory unit 340 for each carriage position by taking the first and second derivatives, respectively, of each carriage position with respect to time.

Using the equation for engagement time T, set out above, and the predefined values for the fusion bonding process to be simulated, the processor/memory unit 340 determines the engagement time T, which is equal to one half of the total time period 2T that a given point site $W_{PS}$ on a workpiece sample S is engaged during the engagement and disengagement segments. The engagement time T is equal to the time period $T_1$ for the engagement segment as well as the time period $T_2$ for the disengagement segment, i.e., the time period for the engagement segment is equal to the time period for the disengagement segment. The time period $T_1$ for the engagement segment and the time period $T_2$ for the disengagement segment are then divided into a plurality of equal discrete time intervals, each of which has a period calculated as discussed above. For each time interval of the engagement and disengagement segments, a protuberance position P is calculated by the processor/memory unit 340 using the following equations:

$$P(i) = G + Di \cdot \left[1 - \cos\left[a\cos\left(1 - \frac{E_M}{Di}\right) \cdot \left(\frac{t}{T} - 1\right)\right]\right]$$

where:

P(i)=position during the engagement segment;

$E_M$ is equal to the amount by which the point site $W_{PS}$ is compressed by the protuberance 25 and the corresponding section 24a of the second roll 24 or the amount by which the point site $W_{PS}$ is compressed by the protuberance 202 and the outer surface 102 of the first plate;

Di is equal to the diameter of the first and second rolls 22 and 24;

t is equal to 0 to $T_1$, where $T_1$ is equal to the total time during the engagement segment;

T is equal to one-half of the total engagement time that a point site $W_{PS}$ on the workpiece sample S is engaged by the protuberance 202 on the second plate 200 and outer surface 102 on the first plate 100 and;

and G is equal to the final compressed thickness of the workpiece sample point site $W_{PS}$.

$$P(o) = G + Di \cdot \left[1 - \cos\left[a\cos\left(1 - \frac{E_M}{Di}\right) \cdot \left(\frac{t}{T} - 1\right)\right]\right]$$

where:

P(0)=position during the disengagement segment;

$E_M$ is equal to the amount by which the point site $W_{PS}$ is compressed by the protuberance 25 and the corresponding section 24a of the second roll 24 and is also equal to the amount by which the point site $W_{PS}$ is compressed by the protuberance 202 and the outer surface 102 of the first plate;

Di is equal to the diameter of the first and second rolls 22 and 24;

t is equal to $T_1$ to $(T_1+T_2)$, where $T_2$ is equal to the total time during the disengagement segment;

T is equal to one-half of the total engagement time that a point site $W_{PS}$ on the workpiece sample S is engaged by the protuberance 202 on the second plate 200 and outer surface 102 on the first plate 100 and;

and G is equal to the final compressed thickness of the workpiece sample point site $W_{PS}$.

From each calculated protuberance position P, the processor/memory unit 340 determines a corresponding carriage position. The processor/memory unit 340 also determines for each discrete time interval of the engagement segment a protuberance velocity and a protuberance acceleration, as noted above. It further determines for each discrete time interval of the disengagement segment a protuberance velocity and a protuberance acceleration, as noted above. The processor/memory unit 340 then provides the discrete time intervals and corresponding carriage positions, protuberance velocities and protuberance accelerations to the motor controller 300, which stores the information in memory.

Once the carriage 30 reaches a position where the protuberance 202 is spaced from the first plate outer surface 102 a distance equal to the maximum workpiece sample thickness of a workpiece capable of being tested, the controller 300 causes the servo linear motors 40 to continue to drive the carriage 30 toward the first plate 100 such that the second plate protuberance 202 and the first plate outer surface 102 engage and compress a point site $W_{PS}$ on the workpiece sample S to a desired final thickness G. In generating appropriate drive signals to the amplifiers 360a, 360b, the controller 300 takes into consideration position feedback information from the linear encoder read head 410 such that it compares the actual position of the carriage 30 determined from the position information provided by the read head 410 to the predefined, desired positions. The controller 300 also takes into consideration force information generated by the load cells 84 in generating appropriate drive signals to the amplifiers 360a, 360b.

When a workpiece sample S is not provided between the plates 100 and 200, and the second plate 200 is moved such that its protuberance 202 is located at a desired inward-most position relative to the first plate outer surface 102, carriage position can be accurately controlled to a tolerance of about +/−10 microns without requiring force feedback information from the load cells 84. This is because no force is applied by the second plate 200 to the first plate 100 during the engagement and disengagement segments since the protuberance 202 never contacts the first plate outer surface 102 or a workpiece sample S even though the protuberance 202 moves to the desired inward-most position relative to the first plate outer surface 102. When a workpiece sample S is provided, a load is generated during engagement of the workpiece sample S by the protuberance 202 and the first plate outer surface 102. This load should be offset by the motors 40 so as to achieve accurate carriage position control to a small tolerance such as from about +/−10 microns to about +/−35 microns. Hence, the controller 300 increases the drive signal provided to the amplifiers 360a, 360b so that the force generated by the motors 40 to the carriage 30 is increased by an amount substantially equal to the magnitude of the force sensed by the load cells 84.

Figure 9B:
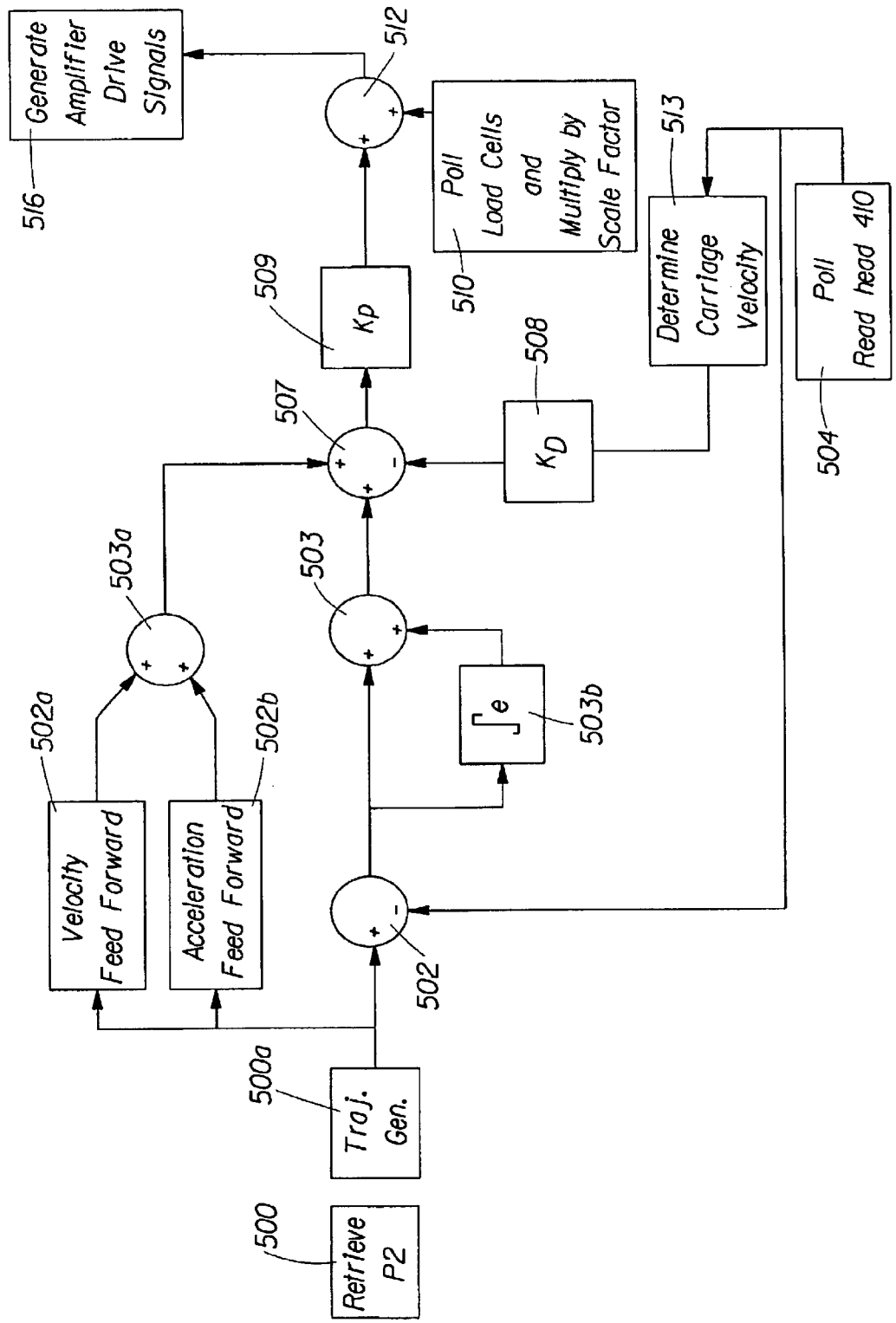
FIG. 9B is a block diagram illustrating steps taken by a controller of the apparatus of FIG. 1 in processing force feedback from load cells while controlling the position of the carriage as a function of time.

A characteristic block diagram is illustrated in FIG. 9B showing steps taken by the controller 300 in accordance with a servo-controller algorithm involving processing force feedback from the load cells 84 while controlling the position of the carriage 30 as a function of time.

At step 500, the controller 300 retrieves serially the desired carriage positions $P_2$, predetermined by the processor/memory unit 340 and previously provided to the controller 300, for the discrete time intervals occurring during each segment. Each of the discrete time intervals occurring during each segment comprises the same first time period $TP_1$. During step 500a, termed a "trajectory generator" step, the controller 300 interpolates between the carriage positions $P_2$, i.e., coarse carriage positions, generated at the discrete time intervals, each comprising the first period $TP_1$, such that fine carriage positions $P_{2F}$ are generated at second time intervals, each comprising a second time period $TP_2$, which is less than the first period $TP_1$.

At step 502, the controller 300 generates a position error value by comparing the fine carriage positions $P_{2F}$ to measured carriage positions. Each measured carriage position is determined using data acquired by polling the linear encoder read head 410, see step 504. At step 503, the current position error is combined, via addition, with its integrated value determined during step 503b. The integration of the position error occurring during step 503b provides a method by which the controller 300 can force the position error to zero, i.e., the controller 300 continuously accumulates the position error and adds the accumulated error back into the current position error.

The fine carriage positions $P_{2F}$ determined during step 500a are used in step 502a to generate a velocity feedforward signal. During step 502a, the controller 300 determines the first derivative of the fine carriage positions $P_{2F}$ with respect to the time base of the servo-controller algorithm, which time base comprises discrete time intervals, each having a period equal to the second period $TP_2$ noted above. The velocity feedforward signal is typically used to compensate for mechanical damping, i.e., friction, present in the apparatus 10. The fine carriage positions $P_{2F}$ determined during step 500a are also used in step 502b to generate an acceleration feedforward signal, wherein the controller 300 takes the second derivative of the fine carriage positions $P_{2F}$ with respect to the time base of the servo-controller algorithm, which time base comprises discrete time intervals, each having a period equal to the second period $TP_2$ noted above. The acceleration feedforward signal is typically used to compensate for the system inertia. At step 503a the velocity and acceleration feedforward signals are summed together.

The velocity of the carriage 30 is determined during step 513 by taking the first derivative of the actual position values received from the encoder read head 410. The first derivative or carriage velocity values are multiplied by a derivative gain value during step 508 so as to provide damping for stability in the controller 300. At step 507, the output from step 508 is subtracted from the sum determined during step 503 as well as the sum determined during step 503a. The output from step 507 is multiplied by a gain factor during step 509 to provide a desired response for the motors 40, such that the time, overshoot, and general bandwidth of the controller 300 can be adjusted for the desired response. In this case the preferred response regarding movement of the carriage 30 to a desired position $P_2$ consists of minimizing the position error, minimizing overshoot in the positioning of the carriage 30, and achieving the desired position $P_2$ in a minimal amount of time.

The output from step 509 is typically referred to as a current reference value, and normally is provided directly to a motor current generator algorithm in the controller 300, which algorithm comprises a current control loop. However, in accordance with the present invention, the controller 300, at step 510, polls the load cell amplifier 84b and generates a compressive load value directly proportional to the load sensed by the load cells 84, i.e., the compression force applied by the carriage 30 to the workpiece W. The controller 300 then multiplies the compressive load value by a scale factor so as to convert the raw signal from the load cell amplifier 84b to a scaled value representing a motor current directly proportional to the force applied by the motors 40 to the carriage 30 causing the compressive load on the workpiece W. This scaled compressive load value is added to the current reference value at step 512 to generate a value that represents the actual force required by the motors 40 to move the carriage 30 to the next desired position $P_2$, as defined by the output from step 509, as well as the motor force required to generate the compressive load on the workpiece W, as represented by the output from step 510. At step 516, using a current loop, the controller 300 determines an appropriate drive signal for the first and second amplifiers 360a and 360b based on the output from step 512. The current loop is typically configured from the motors' electrical characteristics, and modified so as to provide a desired current response. The desired current response in this embodiment is minimal current overshoot, at the fastest achievable rate to the output from step 512.

By utilizing the scaled compressive load value with the current reference value at step 512, the controller 300 effectively bypasses the position, velocity and acceleration loops in steps 502, 502a and 502b with regard to changes in the load applied by the carriage 30 to the workpiece W so as to more directly take into consideration compressive load variations when determining the drive signals for the first and second amplifiers 360a and 360b, thereby directly enhancing the accuracy of the control of the position of the carriage 30 as a function of time. It is also noted that when the load value is taken into consideration, the controller response time for controlling the operation of the motors 40 and, hence, the position of the carriage 30 as a function of time, is improved. That is, without taking into consideration the load value sensed by the load cells during step 512, changes in the compressive load applied by the workpiece W to the carriage 30, or vice versa, would have to be indirectly taken into consideration by the position, velocity and acceleration control loops. Doing so would reduce the response time of the controller 300 in controlling the operation of the motors 40 such that the accuracy of the control of the carriage position by the controller 300 would be negatively affected, especially at high speeds when the load applied by the workpiece W to the carriage 30 and vice versa changes rapidly.

Linear movement of the second plate 200 relative to the first plate 100 in accordance with the discrete time intervals and corresponding protuberance positions results in work being done to the sample S simulating work which would have been done to the sample S had the sample S passed through a pair of fusion bonding rolls 22, 24 and been engaged by a protuberance 25 on the first roll 22. Controlled movement of the carriage 30 by the controller 300 typically results in the distal end 202a of the protuberance 202 following a position vs. time curve such as the one illustrated in FIG. 10A.

Equations used by the processor/memory unit 340 to determine a carriage position (also referred to herein as "protuberance position") for each discrete time interval, which intervals have the same period as the time intervals corresponding to the engagement and disengagement segments, and other parameters, will be provided for the remaining segments, namely, the forward acceleration segment; the forward linear segment; the forward transition segment; the reverse transition segment; the reverse linear segment; and the reverse acceleration segment. The unit 340 provides the time intervals and corresponding carriage positions to the drive controller 300 for these segments.

Figure 11:
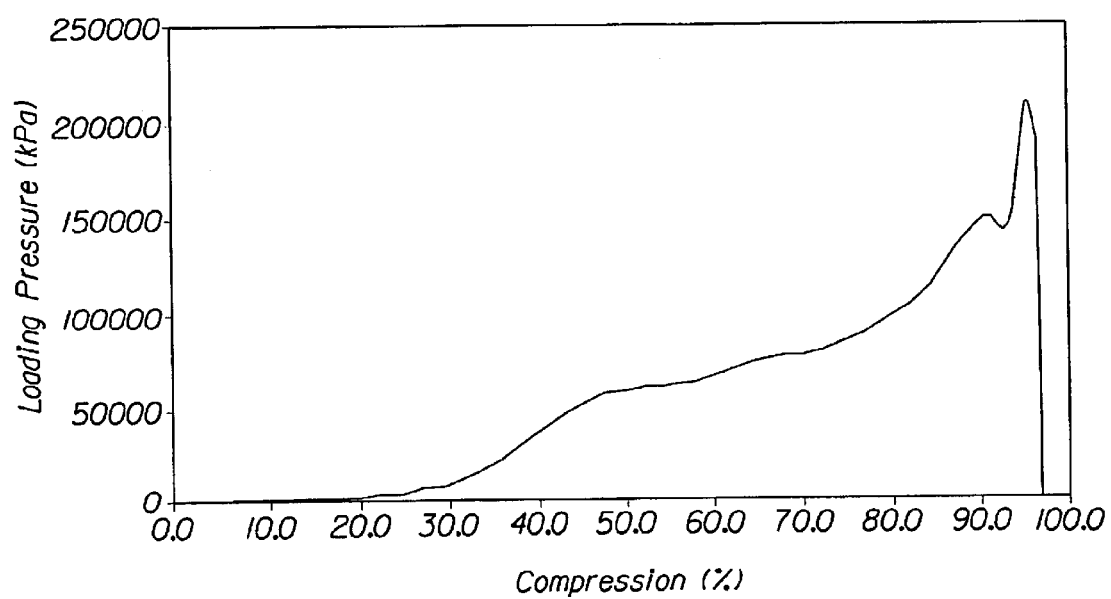
FIG. 11 is a plot of a "Load Per Unit Workpiece Area vs. Percent Compression of the Workpiece Sample" curve.

For the Engagement Segment, an engineer/technician defines a maximum workpiece sample thickness or caliper that the apparatus 10 is capable of testing, and this value is provided to the processor/memory unit 430. The unit 340 determines, via the equation set out above for $T_1$, the time required for the carriage 30 to move from a position where the distal end 202a of the second plate protuberance 202 is positioned the maximum workpiece material thickness or caliper distance away from the first plate outer surface 102 to a position where the protuberance 202 is positioned a desired final distance from the first plate outer surface 102, i.e., where a point site $W_{PS}$ on a sample S is compressed to a desired thickness G. It is noted that a workpiece sample S having a thickness less than the maximum workpiece sample thickness may be tested, see FIG. 11, where the workpiece sample tested had a thickness of 3.5 mm while the maximum material caliper was 6.912 mm. Thereafter, the unit 340 divides the time $T_1$ by the predefined time interval period, i.e., the first time period $TP_1$, which period is determined as set out above, to determine a plurality of discrete time intervals for the Engagement Segment. The unit 340 then determines, for each discrete time interval, a protuberance position P (corresponding to a carriage position relative to the carriage "0 position," where the protuberance distal end 202a makes contact with the first plate outer surface 102), a protuberance velocity (which is equal to the carriage velocity) and a protuberance acceleration (which is equal to the carriage acceleration), in the manner noted above, and see the Example set out below where the total time $T_1$ for the engagement segment is equal to 9.19 milliseconds.

The total time period for the forward transition segment is set to a predefined value, e.g., 3.1 milliseconds and, typically, the same time period is used for this segment during all fusion bonding process simulations. The final protuberance position (corresponds to a final carriage position relative to the carriage "0 position"), final protuberance velocity, and final protuberance acceleration for this segment are all equal to the initial protuberance position, initial protuberance velocity and initial protuberance acceleration for the engagement segment, see the Example set out below. Further, the initial protuberance acceleration for this segment must be 0. From these given values, the unit 340 determines initial and intermediate protuberance positions, initial and intermediate protuberance velocity values, and initial and intermediate protuberance acceleration values for this segment.

During the Forward Linear Segment, the protuberance acceleration (corresponds to the carriage acceleration) decreases to zero such that the protuberance velocity is maintained at a constant value. This segment is used to buffer any jerking motion of the carriage 30 as it changes from a positive acceleration to a negative acceleration. The time period for this segment is set to a predefined value, e.g., 2.0 milliseconds, and typically the same time period is used for this segment during all fusion bonding process simulations. The final protuberance acceleration must be equal to zero and the final protuberance velocity must equal the initial protuberance velocity for the Forward Transition Segment, see the Example set out below.

During the Forward Acceleration Segment, the carriage 300 accelerates at a constant rate from a 0 velocity starting at a home position to a final velocity, which is equal to the initial velocity of the Forward Linear Segment. The carriage home position is defined by an engineer/technician and is relative to the carriage "0 position." Typically, it is equal to or nearly equal to the maximum distance the carriage 30 may be positioned away from its "0 position." In the Example set out below, it is set at 75 mm. The distance for this segment is equal to the distance the home position is spaced from the carriage "0 position" minus the summation of the distances the carriage 30 moves during the Forward Linear and Forward Transition Segments and the maximum workpiece sample thickness. The time for this segment is not predefined. The unit 340 determines a positive constant acceleration (i.e., a protuberance acceleration) required for the carriage 30 to be accelerated from a 0 velocity to a velocity equal to the initial protuberance velocity for the Forward Linear Segment within the predefined distance for this segment.

For the Disengagement Segment, the processor/memory unit 340 initially determines, via the equation set out above for $T_2$, the time required for the carriage 30 to move from its position where the protuberance 202 on the second plate 200 is at its maximum engagement depth with the point site $W_{PS}$ on the workpiece sample S to a position where the protuberance 202 is spaced a distance from the first plate outer surface 102 equal to maximum workpiece sample thickness or caliper that the apparatus 10 is capable of testing. Thereafter, the unit 340 divides the time $T_2$ by the predefined time interval period, i.e., the first time period $TP_1$, which period is determined as set out above, to determine a plurality of discrete time intervals for the Disengagement Segment. The unit 340 then determines, for each discrete time interval, a protuberance position P (equal to the carriage position from the "0 position"), a protuberance velocity (which is equal to the carriage velocity) and protuberance acceleration (which is equal to the carriage acceleration), in the manner discussed above and see the Example set out below where the total time $T_2$ for this segment is equal to 9.19 milliseconds.

The total time period for the Reverse Transition Segment is set to a predefined value, e.g., 3.1 milliseconds and, typically, the same time period is used for this segment during all fusion bonding process simulations. The initial protuberance position, initial protuberance velocity, and initial protuberance acceleration (In the Example and for the Reverse Transition Segment, Reverse Acceleration Segment and the Disengagement Segment, a positive acceleration has a negative value and a negative acceleration has a positive value) for this segment are all equal to the final protuberance position, final protuberance velocity and final protuberance acceleration for the Disengagement Segment, see the Example set out below. Further, the final protuberance acceleration must be 0 at the end of the Reverse Transition Segment. From these given values, the unit 340 determines initial and intermediate protuberance positions, initial and intermediate protuberance velocity values and initial and intermediate protuberance acceleration values for this segment.

During the Reverse Linear Segment, the protuberance acceleration is zero. This segment is used to buffer any jerking motion of the carriage 30 as it changes from a negative acceleration to a positive acceleration. The time period for this segment is set to a predefined value, e.g., 2.0 milliseconds, and typically, is the same time period used for this segment during all fusion bonding process simulations. The initial tooth tip velocity for this segment must equal the final tooth tip velocity for the Reverse Transition Segment, see the Example set out below.

During almost the entirety of the Reverse Acceleration Segment, the carriage 300 decelerates at a constant rate from an initial velocity equal to the final velocity of the Reverse Linear Segment down to a 0 velocity, at which point the carriage is at its home position. The distance for this segment is equal to the distance the home position is spaced from the carriage "0 position" minus the summation of the distances the carriage 30 moves during the Reverse Linear and Reverse Transition Segments and the maximum workpiece sample thickness. The time period for this segment is not predefined. The unit 340 determines a constant rate of deceleration (i.e., a protuberance deceleration) required for the carriage 30 to be decelerated from a velocity equal to the final protuberance velocity for the Reverse Linear Segment to a 0 velocity within the predefined distance for this segment.

The processor/memory unit 340 determines protuberance positions, i.e. carriage positions, for each of the equal discrete time intervals as well as other parameters for the forward acceleration segment; the forward linear segment; the forward transition segment; the reverse transition segment; the reverse linear segment; and the reverse acceleration segment using the following equations:

Tfl=Time in the Forward Linear Segment; Predefined value, e.g., 0.0020 second;

Tft=Time in the Forward Transition Segment; Predefined value, e.g., 0.0031 second;

Tbl=Time in the Reverse (Backward) Linear Segment; Predefined value, e.g., 0.0020 second;

Tbt=Time in the Reverse (Backward) Transition Segment; Predefined value, e.g., 0.0031 second;

$E_M$ is equal to the initial thickness $M_T$ of the workpiece sample S minus the final thickness G of a point site $W_{PS}$ on the sample;

Di is equal to the diameter of the first and second rolls 22, 24 (it is presumed that the rolls 22, 24 have the same diameter);

and Vw is equal to the workpiece velocity;

Plim=Is equal to the distance between the carriage home position and the carriage 0 position;

$T=T_1=T_2$; and

Npts=Total number of control points, all of the same period, during all segments, e.g., 7990.

Initial velocity in the forward transition segment (n/sec)

$$Vftl = Vil - \frac{Ail \cdot Tft}{2}$$

Jerk in the forward transition segment (m/sec³)

$$Kf = \frac{(Ail - 0)}{Tft}$$

Initial position in the forward transition segment (m)

$$Pft1 = Pi1 - Vft1 \cdot Tft - \frac{Kf \cdot Tft^3}{6}$$

Initial position in the forward linear segment (m)

$$Pfl1 = Pft1 - Vft1 \cdot Tfl$$

Time in forward acceleration segment (sec)

$$Tfa = \frac{(Pfl1 - P\lim)}{\frac{Vft1}{2}}$$

Acceleration in forward acceleration segment (m/sec²)

$$Afa = \frac{(Vft1 - 0)}{Tfa}$$

Total time in forward segments (sec)

$$Tf = T_1 + Tft + Tfl + Tfa$$

Total time in forward acceleration and forward linear segments $$Tfal = Tfa + Tfl$$

Total time in the forward acceleration, forward linear and forward transition segments (sec)

$$Tfalt = Tfa + Tfl + Tft$$

Final disengagement position (m)

$$Po2 = G + Di \cdot \left[1 - \cos\left[a\cos\left(1 - \frac{E_M}{Di}\right) \cdot (1)\right]\right]$$

Final disengagement velocity (m/sec)

$$Vo2 = +Di \cdot \sin\left[a\cos\left(1 - \frac{E_M}{Di}\right) \cdot (1)\right] \cdot \left[\frac{a\cos\left(1 - \frac{E_M}{Di}\right)}{T}\right]$$

Final disengagement acceleration (m/sec²)

$$Ao2 = +Di \cdot \cos\left[a\cos\left(1 - \frac{E_M}{Di}\right) \cdot (1)\right] \cdot \left[\frac{a\cos\left(1 - \frac{E_M}{Di}\right)}{T}\right]^2$$

Jerk in the backward transition segment (m/sec³)

$$Kb = \frac{(0 - Ao2)}{Tbt}$$

Final position in the backward transition segment (m)

$$Pbt2 = Po2 + Vo2 \cdot Tbt + \frac{(Ao2 \cdot Tbt^2)}{2} + \frac{(Kb \cdot Tbt^3)}{6}$$

Final velocity in the backward transition segment (m)

$$Vbt2 = Vo2 + \frac{Ao2}{2} \cdot Tbt$$

Final position in the backward linear position (m)

$$Pbl2 = Pbt2 + Vbt2 \cdot Tbl$$

Time in the backward acceleration segment (sec)

$$Tba = \frac{(P\lim - Pbl2)}{\left(\frac{Vbt2}{2}\right)}$$

Acceleration in the backward acceleration segment (m/sec²)

$$Aba = \frac{(0 - Vbt2)}{Tba}$$

Total time in the forward segments and disengagement segment (sec)

$$Tbo = Tf + T_2$$

Total time in the forward segments plus the disengagement and backward transition segments (sec)

$$Tbot = Tf + T_2 + Tbt$$

Total time in the forward segments plus the disengagement, backward transition and backward linear segments (sec)

$$Tbotl = Tf + T_2 + Tbt + Tbl$$

Total time in the forward and backward segments (sec)

$$Tfb = Tf + T_2 + Tbt + Tbl + Tba$$

Time period per process control point (sec)

$$Tspl = \frac{Tfb}{Npts}$$

Position in forward acceleration segment (m); where t=0 to Tfa (sec)

$$Pfa = P\lim + \frac{Afa \cdot t^2}{2}$$

Position in forward linear segment (m); where t=0 to Tfl (sec)

$$Pfl = Pfl1 = Vft1 \cdot t$$

Position in forward transition segment (m); where t=0 to Tft (sec)

$$Pft = Pft1 + Vft1 \cdot t + \frac{Kf \cdot t^3}{6}$$

Position in engagement segment (m); where t=0 to $T_1$ (sec)

$$Pi = G + Di \cdot \left[1 - \cos\left[a\cos\left(1 - \frac{E_M}{Di}\right) \cdot \left(\frac{t}{T} - 1\right)\right]\right]$$

Position in disengagement segment (m); where t=$T_1$ to ($T_1+T_2$) (sec)

$$Po = G + Di \cdot \left[1 - \cos\left[a\cos\left(1 - \frac{E_M}{Di}\right) \cdot \left(\frac{t}{T} - 1\right)\right]\right]$$

Position in backward transition segment (m); where t=0 to Tbt (sec)

$$Pbt = Po2 + Vo2 \cdot t + \frac{Ao2 \cdot t^2}{2} + \frac{Kb \cdot t^3}{6}$$

Position in backward linear segment (m); where t=0 to Tbl (sec)

$$Pbl = Pbt2 + Vbt2 \cdot t$$

Position in backward acceleration segment (m); where t=0 to Tba (sec)

$$Pba = Pbl2 + Vbt2 \cdot t + \frac{Aba \cdot t^2}{2}$$

Prior to conducting a test operation, the controller 300 controls the movement of the second plate 200 so that it slowly moves toward the first plate 100 until its protuberance 202 engages the first plate outer surface 102. At the point of engagement, a position error of the servo linear motors 40 increases because movement of the carriage 30 is blocked by the engagement between the protuberance 202 and the first plate outer surface 102, which increase in position error is detected by the controller 300. That is, the controller 300 determines from position signals generated by the linear encoder read head 410 that the position of the carriage 30 is not changing even though the controller 300 is generating a drive signal to provide power to the motors 40. In response to sensing 0 movement of the carriage 30, the controller 300 knows that the carriage 30 is positioned at a "0 position" for the carriage 30, i.e., the position of the carriage 30 where the protuberance 202 is in engagement with the first plate outer surface 102. The controller 300, based upon a position signal generated by the linear encoder read head 410 after reading the corresponding position value from the sensor strip 412, defines the current position of the carriage 30 as being at the carriage "0 position."

Figure 10A:
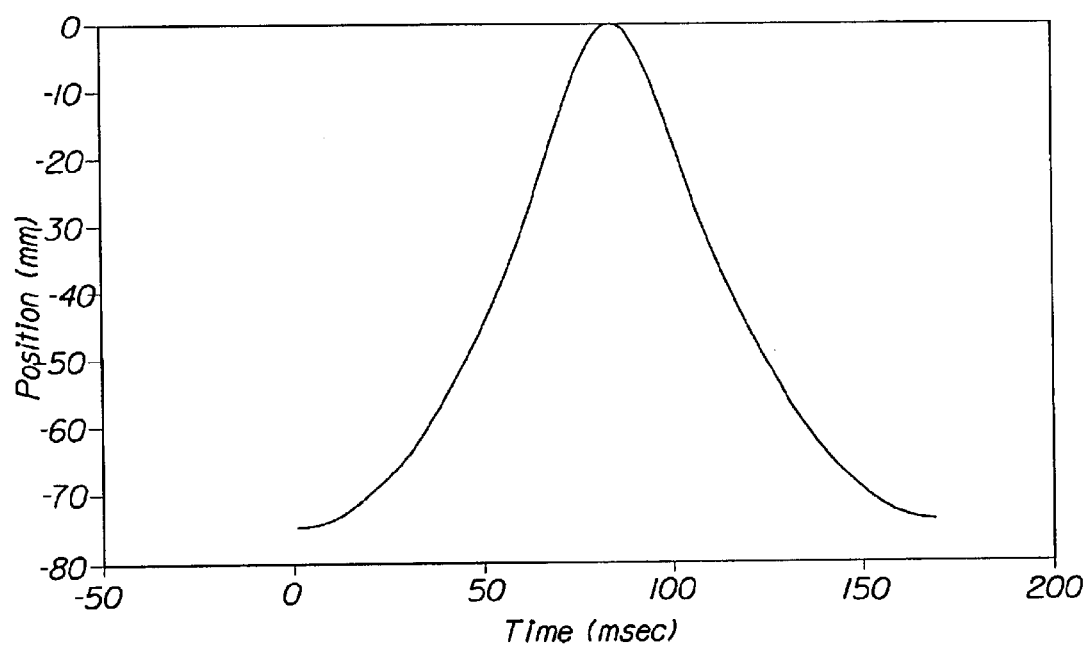
FIG. 10A is a plot of a position by time profile for the Example.
Figure 10B:
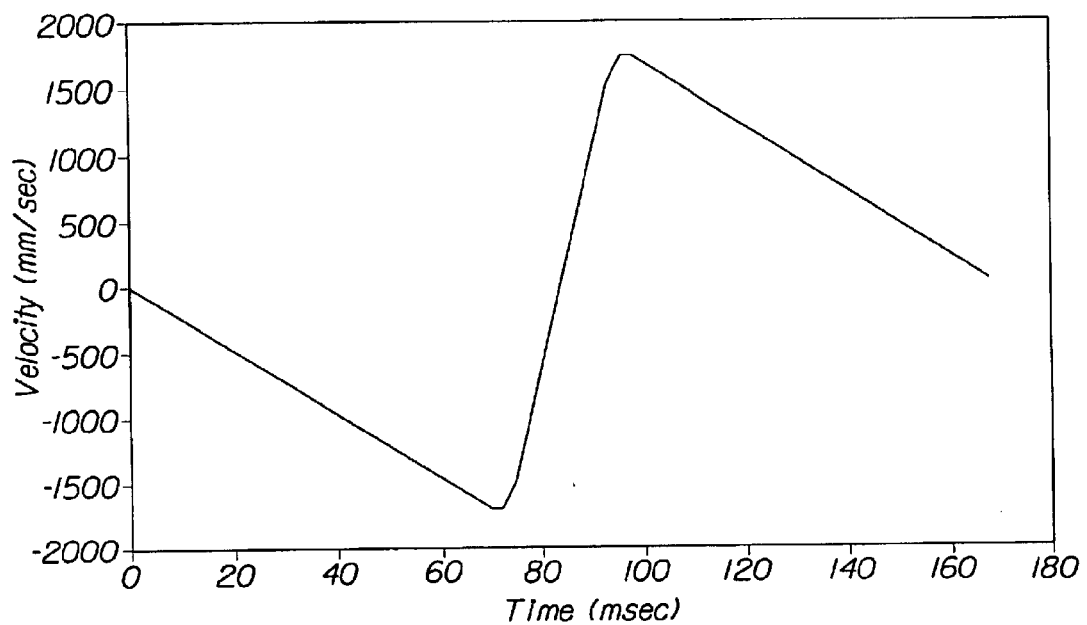
FIG. 10B is a plot of a velocity by time profile for the Example.
Figure 10C:
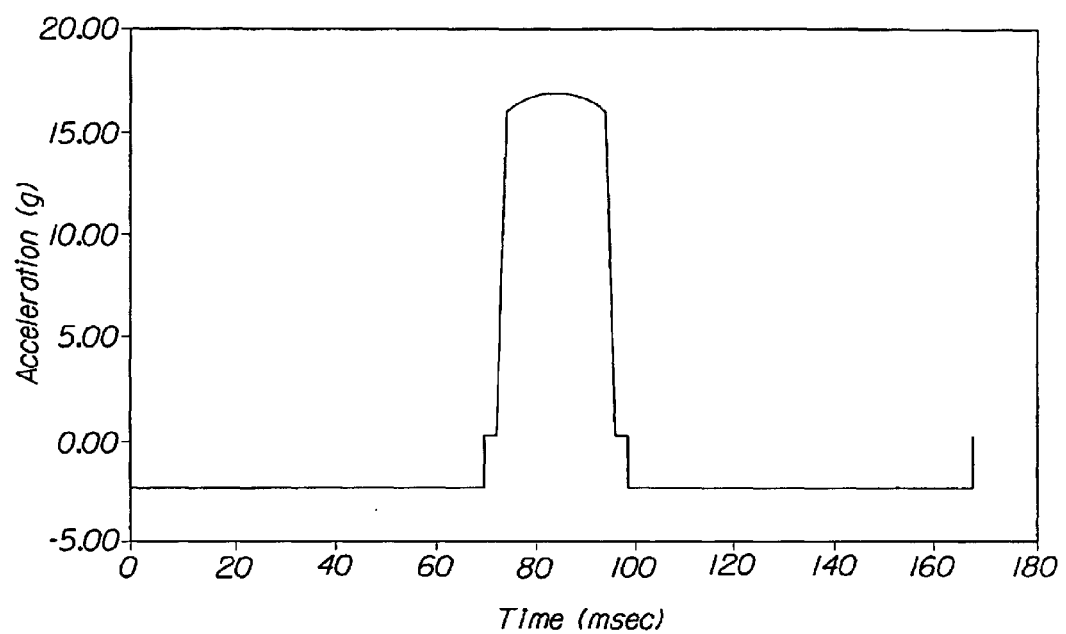
FIG. 10C is a plot of an acceleration by time profile for the Example.

Data from an Example fusion roll simulation operation is set out below. A position by time profile for the Example is illustrated in FIG. 10A; a velocity by time profile for the Example is illustrated in FIG. 10B; and an acceleration by time profile for the Example is illustrated in FIG. 10C (1 g=9.8 m/s$^2$).

As illustrated in FIGS. 5 and 8, the apparatus 10 further comprises four electromicrometer sensors 104 coupled to the first plate 100 so as to sense the distance between the first plate outer surface 102 and the second plate outer surface 204 during a fusion bonding simulation operation, i.e., a workpiece point site compression operation. The sensors 104 are commercially available from Kaman Aerospace Corporation, Middletown, Conn. under the product designation 8000 series and are capable of sensing the distance between the outer surfaces 102 and 204 to an accuracy of +/−0.5 micron. Signals generated by the sensors 104 are provided to the drive controller 300 which, in turn, forwards corresponding signals to the processor/memory unit 340 along with load cell data, carriage position data and discrete time interval data.

In the illustrated embodiment, signals output by the sensors 104 are not used by the drive controller 300 to control the operation of the motors 40. However, the processor/memory unit 340 uses the information generated by the sensors 104 in generating a "Load Per Unit Workpiece Point Site Area vs. Percent Compression of the Workpiece Sample" curve for a completed workpiece point site compression operation. In particular, the unit 340 uses the information generated by the sensors 104 for the segment of the point site compression test corresponding to when the distal end 202a of the second plate protuberance 202 is in the range of approximately 1.0 mm away from the outer surface 102 of the first plate 100 to a distance away from the outer surface 102 equal to the final compressed thickness G of the workpiece sample S. When the distal end 202a of the second plate protuberance 202 is located more than 1.0 mm away from the first plate outer surface 102, the processor/memory unit 340 uses carriage positions calculated in the manner discussed below in determining the curve.

When the distal end 202a of the protuberance 202 is within the range of $M_T$, which is equal to the initial thickness of the workpiece sample, to 1.0 mm, or some other predetermined distance, away from the first plate outer surface 102, workpiece percent compression is determined from the following equation:

Percent Compression=$([M_T-P(t)]/M_T) \times 100[\{]ps$ where $M_T$=the initial thickness of the workpiece sample; and P(t)=to the carriage position relative to the carriage "0 position," where the protuberance distal end 202a makes contact with the first plate outer surface 102, and is determined using the following equation:

$$P(t) = G + Di \cdot \left[1 - \cos\left[a\cos\left(1 - \frac{E_M}{Di}\right) \cdot \left(\frac{t}{T} - 1\right)\right]\right] \quad \text{Eq. A}$$

wherein $E_M$ is equal to the final amount by which the point site is compressed by the protuberance 202 on the second plate 200 and an outer surface 102 of the first plate 100;

G is equal to the desired final compressed thickness of the workpiece sample;

Di is equal to the diameter of first and second rolls;

t is equal to the process time and has a value from 0 to ($T_1+T_2$); and $T=T_1=T_2$ is equal to one-half of the total time the workpiece point site is engaged by the protuberance 202 on the second plate 200 and the outer surface 102 of said first plate 100.

When the distal end 202a of the protuberance 202 is within the range of 1.0 mm, or some other predefined distance, away from the first plate outer surface 102 to a distance away from the first plate outer surface 102 equal to the final compressed thickness G of the workpiece sample S, workpiece percent compression is determined from the following equation:

Percent Compression=$([M_T-S(t)]/M_T) \times 100\%$ wherein $M_T$=the initial thickness of the workpiece sample;

S(t)=the distance between the protuberance distal end 202a and the first plate outer surface 102 determined using signals generated by the four electromicrometer sensors 104.

The "Load Per Unit Workpiece Point Site Area" for each time interval of the engagement and disengagement segments is determined using the load cell data divided by the outer surface area of the protuberance distal end 202a. The processor/memory unit 340 presumes that the protuberance 202 has engaged the workpiece sample S when the protuberance distal end 202a, i.e., the carriage position, is positioned a distance away from the first plate outer surface 102 equal to the initial thickness of the workpiece sample, which distance is determined from the linear encoder read head data. A "Load Per Unit Workpiece Point Site Area vs. Percent Compression of the Workpiece Sample" curve corresponding to the Example set out below and for a polyethylene workpiece having a thickness or caliper of 3.5 mm is found in FIG. 11.

In accordance with another embodiment of the present invention, percent compression of the workpiece sample is determined without using data from four electromicrometer sensors 104. Instead, a single spring constant for the deflecting mechanical elements including the combination of springs 74 is determined, such as by causing the protuberance 202 to engage the first plate outer surface 102 and taking the ratio of the force sensed by the load cells 84 to the distance moved by the protuberance 202, after engagement with the outer surface 102, as sensed by the linear encoder read head 410. After load data, generated by the load cells 84, has been stored following a workpiece point site compression test operation, that load cell data is divided by the spring constant so as to determine first plate deflection data $D_L$. Thereafter, percent compression of the workpiece sample is determined from the following equation:

$$\{[M_T-(P(t)-D_L)]/M_T\} \times 100\%$$

where $M_T$ the initial thickness of the workpiece sample;
P(t) is equal to the carriage positions determined using equation (A) above; and
$D_L$ is equal to the first plate deflection data.

The "Load Per Unit Workpiece Point Site Area" is determined using the load cell data divided by the outer surface area of the protuberance distal end 202a as noted above.

| DATA FROM EXAMPLE | |
|---|---|
| Maximum Material Caliper, $M_T$ (mm) | 6.912 |
| Gap Between Rolls, G (mm) | 0.1 |
| Engagement Distance, $E_M$ (mm) | 6.812 |
| Roll Diameter, Di (mm) | 152.40 |
| Web Speed, $V_W$ (m/sec) | 2.4890 |
| Home Position, Plim (mm) | 75.0 |
| Time in Forward Linear Segment, Tfl (msec) | 2.0 |
| Time in Reverse Linear Segment, Tbl (msec) | 2.0 |
| Time in Forward Transition Segment, Tft (msec) | 3.1 |
| Time in Reverse Transition Segment, Tbt (msec) | 3.1 |
| Jerk in Forward Transition Segment, Kf (mm/sec^3) | 5.01E+07 |
| Jerk in Forward Reverse Segment, Kb (mm/sec^3) | −5.01E+07 |
| Gravitational Acceleration, g (mm/sec2) | 9814.56 |

Forward Acceleration Segment

| Acceleration Time (msec) | Acceleration Distance (mm) | Total Time (msec) | Ram Position (mm) | Ram Velocity (mm/sec) | Ram Acceleration (mm/sec^2) | Ram Acceleration (g's) |
|---|---|---|---|---|---|---|
| 0.00 | 0.00 | 0.00 | 75.000 | 0.00 | 0 | 0.00 |
| 0.10 | 0.000 | 0.10 | 75.000 | −2 | −24599 | −2.51 |
| 6.96 | −0.596 | 6.96 | 74.404 | −171 | −24599 | −2.51 |
| 13.92 | −2.384 | 13.92 | 72.616 | −342 | −24599 | −2.51 |
| 20.88 | −5.364 | 20.88 | 69.636 | −514 | −24599 | −2.51 |
| 27.85 | −9.537 | 27.85 | 65.463 | −685 | −24599 | −2.51 |
| 34.81 | −14.901 | 34.81 | 60.099 | −856 | −24599 | −2.51 |
| 41.77 | −21.457 | 41.77 | 53.543 | −1027 | −24599 | −2.51 |
| 48.73 | −29.206 | 48.73 | 45.794 | −1199 | −24599 | −2.51 |
| 55.69 | −38.146 | 55.69 | 36.854 | −1370 | −24599 | −2.51 |
| 62.65 | −48.279 | 62.65 | 26.721 | −1541 | −24599 | −2.51 |
| 69.61 | −59.603 | 69.61 | 15.397 | −1712 | −24599 | −2.51 |

Forward Linear Segment

| Linear Time (msec) | Acceleration Distance (mm) | Total Time (msec) | Ram Position (mm) | Ram Velocity (mm/sec) | Ram Acceleration (mm/sec^2) | Ram Acceleration (g's) |
|---|---|---|---|---|---|---|
| 0.00 | 0.000 | 69.61 | 15.397 | −1712 | −24599 | −2.51 |
| 0.01 | −0.017 | 69.62 | 15.379 | −1712 | 0 | 0.00 |
| 0.20 | −0.342 | 69.81 | 15.054 | −1712 | 0 | 0.00 |
| 0.40 | −0.685 | 70.01 | 14.712 | −1712 | 0 | 0.00 |
| 0.60 | −1.027 | 70.21 | 14.369 | −1712 | 0 | 0.00 |
| 0.80 | −1.370 | 70.41 | 14.027 | −1712 | 0 | 0.00 |
| 1.00 | −1.712 | 70.61 | 13.684 | −1712 | 0 | 0.00 |
| 1.20 | −2.055 | 70.81 | 13.342 | −1712 | 0 | 0.00 |
| 1.40 | −2.397 | 71.01 | 12.999 | −1712 | 0 | 0.00 |
| 1.60 | −2.740 | 71.21 | 12.657 | −1712 | 0 | 0.00 |

-continued

DATA FROM EXAMPLE

| | | | | | | |
|---|---|---|---|---|---|---|
| 1.80 | −3.082 | 71.41 | 12.314 | −1712 | 0 | 0.00 |
| 2.00 | −3.425 | 71.61 | 11.972 | −1712 | 0 | 0.00 |

Forward Transition Segment

| Transition Time (msec) | Transition Distance (mm) | Total Time (msec) | Ram Position (mm) | Ram Velocity (mm/sec) | Ram Acceleration (mm/sec^2) | Ram Acceleration (g's) |
|---|---|---|---|---|---|---|
| 0.00 | 0.000 | 71.61 | 11.972 | −1712 | 0 | 0.00 |
| 0.31 | −0.531 | 71.92 | 11.441 | −1688 | 15533 | 1.58 |
| 0.62 | −1.060 | 72.23 | 10.912 | −1664 | 31067 | 3.17 |
| 0.93 | −1.586 | 72.54 | 10.386 | −1640 | 46600 | 4.75 |
| 1.24 | −2.107 | 72.85 | 9.864 | −1616 | 62133 | 6.33 |
| 1.55 | −2.623 | 73.16 | 9.349 | −1592 | 77667 | 7.91 |
| 1.86 | −3.131 | 73.47 | 8.840 | −1568 | 93200 | 9.50 |
| 2.17 | −3.631 | 73.78 | 8.341 | −1544 | 108734 | 11.08 |
| 2.48 | −4.119 | 74.09 | 7.852 | −1520 | 124267 | 12.66 |
| 2.79 | −4.596 | 74.40 | 7.375 | −1496 | 139800 | 14.24 |
| 3.10 | −5.060 | 74.71 | 6.912 | −1472 | 155334 | 15.83 |

Engagement Segment

| Engagement Time (msec) | Engagement Distance (mm) | Total Time (msec) | Ram Position (mm) | Ram Velocity (mm/sec) | Ram Acceleration (mm/sec^2) | Ram Acceleration (g's) |
|---|---|---|---|---|---|---|
| 0 | 0.000 | 74.71 | 6.912 | −1472 | 155334 | 15.83 |
| 0.92 | −1.286 | 75.63 | 5.626 | −1328 | 156706 | 15.97 |
| 1.84 | −2.441 | 76.55 | 4.471 | −1184 | 157937 | 16.09 |
| 2.76 | −3.461 | 77.47 | 3.451 | −1038 | 159027 | 16.20 |
| 3.68 | −4.348 | 78.39 | 2.564 | −892 | 159973 | 16.30 |
| 4.59 | −5.099 | 79.31 | 1.813 | −744 | 160774 | 16.38 |
| 5.51 | −5.715 | 80.23 | 1.197 | −596 | 161431 | 16.45 |
| 6.43 | −6.195 | 81.14 | 0.717 | −448 | 161943 | 16.50 |
| 7.35 | −6.538 | 82.06 | 0.374 | −299 | 162309 | 16.54 |
| 8.27 | −6.743 | 82.98 | 0.169 | −149 | 162528 | 16.56 |
| 9.19 | −6.812 | 83.90 | 0.100 | 0 | 162602 | 16.57 |

Disengagement Segment

| Engagement Time (msec) | Engagement Distance (mm) | Total Time (msec) | Ram Position (mm) | Ram Velocity (mm/sec) | Ram Acceleration (mm/sec^2) | Ram Acceleration (g's) |
|---|---|---|---|---|---|---|
| 0.00 | 0.000 | 83.90 | 0.100 | 0 | 162602 | 16.57 |
| 0.92 | 0.069 | 84.82 | 0.169 | 149 | 162528 | 16.56 |
| 1.84 | 0.274 | 85.74 | 0.374 | 299 | 162309 | 16.54 |
| 2.76 | 0.617 | 86.66 | 0.717 | 448 | 161943 | 16.50 |
| 3.68 | 1.097 | 87.58 | 1.197 | 596 | 161431 | 16.45 |
| 4.59 | 1.713 | 88.49 | 1.813 | 744 | 160774 | 16.38 |
| 5.51 | 2.464 | 89.41 | 2.564 | 892 | 159973 | 16.30 |
| 6.43 | 3.351 | 90.33 | 3.451 | 1038 | 159027 | 16.20 |
| 7.35 | 4.371 | 91.25 | 4.471 | 1184 | 157937 | 16.09 |
| 8.27 | 5.526 | 92.17 | 5.626 | 1328 | 156706 | 15.97 |
| 9.19 | 6.812 | 93.09 | 6.912 | 1472 | 155334 | 15.83 |

Reverse Transition Segment

| Transition Time (msec) | Transition Distance (mm) | Total Time (msec) | Ram Position (mm) | Ram Velocity (mm/sec) | Ram Acceleration (mm/sec^2) | Ram Acceleration (g's) |
|---|---|---|---|---|---|---|
| 0.00 | 0.000 | 93.09 | 6.912 | 1472 | 155334 | 15.83 |
| 0.31 | 0.463 | 93.40 | 7.375 | 1496 | 139800 | 14.24 |
| 0.62 | 0.940 | 93.71 | 7.852 | 1520 | 124267 | 12.66 |
| 0.93 | 1.429 | 94.02 | 8.341 | 1544 | 108734 | 11.08 |
| 1.24 | 1.928 | 94.33 | 8.840 | 1568 | 93200 | 9.50 |
| 1.55 | 2.437 | 94.64 | 9.349 | 1592 | 77667 | 7.91 |
| 1.86 | 2.952 | 94.95 | 9.864 | 1616 | 62133 | 6.33 |
| 2.17 | 3.474 | 95.26 | 10.386 | 1640 | 46600 | 4.75 |
| 2.48 | 4.000 | 95.57 | 10.912 | 1664 | 31067 | 3.17 |
| 2.79 | 4.529 | 95.88 | 11.441 | 1688 | 15533 | 1.58 |
| 3.10 | 5.060 | 96.19 | 11.972 | 1712 | 0 | 0.00 |

-continued

DATA FROM EXAMPLE

Reverse Linear Segment

| Linear Time (msec) | Acceleration Distance (mm) | Total Time (msec) | Ram Position (mm) | Ram Velocity (mm/sec) | Ram Acceleration (mm/sec^2) | Ram Acceleration (g's) |
|---|---|---|---|---|---|---|
| 0.00 | 0.000 | 96.19 | 11.972 | 1712 | 0 | 0.00 |
| 0.20 | 0.342 | 96.39 | 12.314 | 1712 | 0 | 0.00 |
| 0.40 | 0.685 | 96.59 | 12.657 | 1712 | 0 | 0.00 |
| 0.60 | 1.027 | 96.79 | 12.999 | 1712 | 0 | 0.00 |
| 0.80 | 1.370 | 96.99 | 13.342 | 1712 | 0 | 0.00 |
| 1.00 | 1.712 | 97.19 | 13.684 | 1712 | 0 | 0.00 |
| 1.20 | 2.055 | 97.39 | 14.027 | 1712 | 0 | 0.00 |
| 1.40 | 2.397 | 97.59 | 14.369 | 1712 | 0 | 0.00 |
| 1.60 | 2.740 | 97.79 | 14.712 | 1712 | 0 | 0.00 |
| 1.80 | 3.082 | 97.99 | 15.054 | 1712 | 0 | 0.00 |
| 2.00 | 3.425 | 98.19 | 15.397 | 1712 | 0 | 0.00 |

Reverse Acceleration Segment

| Acceleration Time (msec) | Acceleration Distance (mm) | Total Time (msec) | Ram Position (mm) | Ram Velocity (mm/sec) | Ram Acceleration (mm/sec^2) | Ram Acceleration (g's) |
|---|---|---|---|---|---|---|
| 0.00 | 0.000 | 98.19 | 15.397 | 1712 | 0 | 0.00 |
| 0.10 | 0.171 | 98.29 | 15.568 | 1710 | −24599 | −2.51 |
| 6.96 | 11.325 | 105.15 | 26.721 | 1541 | −24599 | −2.51 |
| 13.92 | 21.457 | 112.11 | 36.854 | 1370 | −24599 | −2.51 |
| 20.88 | 30.398 | 119.07 | 45.794 | 1199 | −24599 | −2.51 |
| 27.85 | 38.146 | 126.03 | 53.543 | 1027 | −24599 | −2.51 |
| 34.81 | 44.703 | 133.00 | 60.099 | 856 | −24599 | −2.51 |
| 41.77 | 50.067 | 139.96 | 65.463 | 685 | −24599 | −2.51 |
| 48.73 | 54.239 | 146.92 | 69.636 | 514 | −24599 | −2.51 |
| 55.69 | 57.219 | 153.88 | 72.616 | 342 | −24599 | −2.51 |
| 62.65 | 59.007 | 160.84 | 74.404 | 171 | −24599 | −2.51 |
| 69.61 | 59.603 | 167.80 | 75.000 | 0 | −24599 | −2.51 |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A simulation press comprising:
   a fixed main body;
   a carriage associated with said main body for movement relative to said main body;
   a first plate coupled to said fixed main body and being adapted to engage a workpiece comprising at least one layer;
   a second plate coupled to said carriage for movement with said carriage, said second plate also being adapted to engage said workpiece;
   at least one motor apparatus coupled to said fixed main body and said carriage for effecting movement of said carriage relative to said main body;
   a drive controller coupled to said at least one motor apparatus for controlling the operation of said at least one motor apparatus in response to feedback from at least one feedback sensor so as to cause said second plate to move relative to said first plate such that said first and second plates engage at least one point site on said workpiece so as to simulate compression loading of a point site on a workpiece in a nip type process.

2. A simulation press as set forth in claim 1, wherein said at least one motor apparatus comprises at least one servo linear motor.

3. A simulation press as set forth in claim 2, wherein said at least one motor apparatus further comprises at least one amplifier which is coupled to said drive controller and said at least one servo linear motor.

4. A simulation press as set forth in claim 1, wherein said carriage reciprocates linearly relative to said fixed main body.

5. A simulation press as set forth in claim 1, wherein said first plate is coupled to said fixed main body via a coupling structure, said coupling structure including at least one force sensor for sensing a force generated during engagement of said workpiece by said first and second plates, said controller increasing a force generated by said at least one motor apparatus in response to a force sensed by said at least one force sensor, said at least one force sensor comprising said at least one feedback sensor.

6. A simulation press as set forth in claim 5, wherein said at least one force sensor comprises at least one load cell.

7. A simulation press as set forth in claim 6, wherein said at least one feedback sensor further comprising a linear encoder read head coupled to said fixed main body and a sensor strip coupled to said carriage, said read head reading position values from said sensor strip and generating corresponding signals to said controller.

8. A simulation press as set forth in claim 7, wherein predetermined discrete time intervals and corresponding carriage positions are provided to said controller and said controller controlling the operation of said at least one motor apparatus so as to control the movement of said carriage based on the carriage positions provided to the controller and in response to the signals generated by said read head and said at least one load cell.

9. A simulation press as set forth in claim 8, wherein at least a portion of said carriage positions are determined via the following equation:

$$P(t) = G + Di \cdot \left[1 - \cos\left[a\cos\left(1 - \frac{E_M}{Di}\right) \cdot \left(\frac{t}{T} - 1\right)\right]\right]$$

wherein
$E_M$ is equal to the amount by which the point site is compressed by a protuberance on the second plate and an outer surface of the first plate;
G is equal to the thickness of the compressed material;
Di is equal to the diameter of first and second rolls;
t is equal to the process time and has a value from 0 to ($T_1+T_2$); and
$T=T_1=T_2$ is equal to one-half of the total time said workpiece point site is engaged by the protuberance on said second plate and the outer surface of said first plate.

10. A simulation press as set forth in claim 6, wherein said fixed main body comprises:
an outer support member;
a pair of L-shaped limiting members associated with said outer support member;
a spring-loading plate; and
a least one adjustment member associated with said outer support member and said spring-loading plate for adjusting the position of said spring-loading plate.

11. A simulation press as set forth in claim 10, wherein said coupling structure comprises:
a spring-loaded plate positioned between said spring-loading plate and said L-shaped limiting members; and
at least one compression spring positioned between said spring-loading plate and said spring-loaded plate for biasing said spring-loaded plate against said L-shaped limiting members.

12. A simulation press as set forth in claim 11, wherein said coupling structure further comprises:
a first cooling plate coupled to said spring-loaded plate;
a first heated plate coupled to said first cooling plate; and
said first workpiece-engaging plate being coupled to said first heated plate.

13. A simulation press as set forth in claim 12, wherein said at least one load cell is positioned between said first cooling plate and said first heated plate.

14. A simulation press as set forth in claim 1, wherein said carriage comprises:
a carriage main body portion;
a second cooling plate coupled to said carriage main body portion;
a second heated plate coupled to said second cooling plate; and
said second workpiece-engaging plate being coupled to said second heated plate.

15. A simulation press as set forth in claim 1, wherein said first workpiece-engaging plate has a substantially planar surface and said second workpiece-engaging plate comprises at least one protuberance and said controller controls the operation of said at least one motor apparatus such that said second plate is moved relative to said first plate so that said protuberance and said planar surface on said first plate engage said point site on said workpiece so as to compress said site to a desired thickness.

16. A simulation press as set forth in claim 15, further comprising at least one sensor associated with one of said first and second plates for sensing the distance between said first and second plates during the workpiece point site compression operation.

17. A simulation press as set forth in claim 16, wherein said at least one sensor comprises at least one electromicrometer coupled to said first plate, said electromicrometer generating signals received by a processor which determines from said signals the distance between a distal end of said protuberance and said first plate planar surface during discrete points of said workpiece point site compression operation.

18. A method of simulating compression loading of a point site on a workpiece in a nip type process comprising the steps of:
providing a workpiece comprising at least one layer;
providing a first plate having a substantially planar surface;
providing a second plate having at least one protuberance; and
moving one of said first and second plates relative to the other of said first and second plates such that said planar surface and said protuberance compress a point site on said workpiece so as to simulate compression loading of a point site on a workpiece in a nip type process.

19. A method of simulating compression loading of a point site on a workpiece in a nip type process as set forth in claim 18 further comprising the steps of:
determining the force generated by said planar surface and said protuberance on said workpiece point site at discrete points;
sensing the distance between said first and second plates at said discrete points during workpiece point site compression; and
determining load per unit area of said workpiece point site as a function of percent compression of said workpiece point site using the determined force and sensed distance at said discrete points.

20. A method of simulating compression loading of a point site on a workpiece in a nip type process as set forth in claim 18, wherein said workpiece comprises at least two layers and said moving step effects fusion bonding of said two or more layers at said workpiece point site.

* * * * *